US010550124B2

(12) United States Patent
Gustafson et al.

(10) Patent No.: US 10,550,124 B2
(45) Date of Patent: Feb. 4, 2020

(54) ATROPISOMERISM FOR INCREASED KINASE INHIBITOR SELECTIVITY

(71) Applicant: SAN DIEGO STATE UNIVERSITY RESEARCH FOUNDATION, San Diego, CA (US)

(72) Inventors: Jeffrey L. Gustafson, San Diego, CA (US); Davis E. Smith, San Diego, CA (US); David Hecht, San Diego, CA (US); Isaac Marquez, San Diego, CA (US); Sean Toenjes, San Diego, CA (US)

(73) Assignee: San Diego State University Foundation, San Diego, CA (US)

( * ) Notice: Subject to any disclaimer, the term of this patent is extended or adjusted under 35 U.S.C. 154(b) by 0 days.

(21) Appl. No.: 15/752,128

(22) PCT Filed: Aug. 15, 2016

(86) PCT No.: PCT/US2016/047085
§ 371 (c)(1),
(2) Date: Feb. 12, 2018

(87) PCT Pub. No.: WO2017/027883
PCT Pub. Date: Feb. 16, 2017

(65) Prior Publication Data
US 2018/0230154 A1     Aug. 16, 2018

Related U.S. Application Data

(60) Provisional application No. 62/204,735, filed on Aug. 13, 2015.

(51) Int. Cl.
*C07D 473/34* (2006.01)
*C07D 487/04* (2006.01)
*A61P 35/02* (2006.01)

(52) U.S. Cl.
CPC ............ *C07D 487/04* (2013.01); *A61P 35/02* (2018.01)

(58) Field of Classification Search
CPC ............................ C07D 487/04; C07D 473/34
See application file for complete search history.

(56) References Cited

U.S. PATENT DOCUMENTS

| | | | | |
|---|---|---|---|---|
| 8,962,831 B2 * | 2/2015 | Goldstein | ............ | C07D 487/04 544/262 |
| 9,540,385 B2 * | 1/2017 | Chen | .................... | A61K 31/519 |
| 9,572,811 B2 * | 2/2017 | Babler | | |
| 2006/0235031 A1 * | 10/2006 | Arnold | ................ | C07D 471/04 514/263.2 |
| 2010/0160356 A1 * | 6/2010 | Heinrich | ............... | C07D 487/04 514/265.1 |
| 2010/0249155 A1 * | 9/2010 | Evarts | ................... | C07D 473/34 514/263.21 |
| 2016/0045503 A1 * | 2/2016 | Goldstein | ............ | C07D 487/04 424/452 |
| 2016/0375026 A1 * | 12/2016 | Chen | .................... | A61K 31/519 514/265.1 |

FOREIGN PATENT DOCUMENTS

| | | | | |
|---|---|---|---|---|
| DE | 102006016426 A1 | 10/2007 | | |
| WO | WO-9610028 A1 * | 4/1996 | ........... | C07D 487/04 |
| WO | 9841525 A1 | 9/1998 | | |
| WO | 2008049047 A2 | 4/2008 | | |
| WO | 2011008302 A1 | 1/2011 | | |
| WO | WO-2015058084 A1 * | 4/2015 | ........... | C07D 487/04 |
| WO | WO 2018237134 A1 * | 12/2018 | | |

OTHER PUBLICATIONS

M. Asif, 6 Heterocyclic Letters (2016) (Year: 2016).*
J. Zhang et al., 9 Nature Reviews Cancer, 28-39 (2009) (Year: 2009).*
D.E. Smith et al., 54 Angewandte Communications, International Edition 11754-11759 (2015) (Year: 2015).*
M.M. Cardenas et al., Organic Letters (2018) (Year: 2018).*
L. M. DeCoen et al., Chemical Reviews (2016) (Year: 2016).*
K. Yoshida et al., Journal of Medicinal Chemistry (2013) (Year: 2013).*
S. R. LaPlante et al., 6 ChemMedChem (2011) (Year: 2011).*
S.R. LaPlante et al., Journal of Medicinal Chemistry (2011) (Year: 2011).*
M.B. Gabra, BCL-2 Inhibitor Scaffolds That are Preorganized Along an Axis of Chirality; The Effect of Atropisomerism on Protein Binding, Master of Science Thesis (May 6, 2015) (Year: 2015).*
Burchat et al., "Pyrrolo[2,3-D]pyrimidines Containing an Extended 5-Substituent as Potent and Selective Inhibitors of Ick II," Bioorg Med Chem Lett., 10(19):2171-2174, Oct. 2000.
Extended Search Report and Written Opinion of the European Patent Office dated Jan. 9, 2019 in EP Application No. 16836030.3 (EP3334430A1); 9pgs.
Smith et al. "Exploiting Atropisomerism to Increase the Target Selectivity of Kinase Inhibitors," Angew Chem Int Ed Engl., 54(40):11754-11759, Sep. 2015.
Barrett et al., "Spontaneous Transfer of Chirality in an Atropisomerically Enriched Two-axis System," Nature, 509:71-75, May 2014.
Bringmann et al., "Atroposelective Synthesis of Axially Chiral Biaryl Compounds," Angew. Chem. Int. Ed. 2005, 44, 5384-5427, Aug. 2005.
Buqué et al., "Molecular Mechanism Implicated in Pemetrexed-induced Apoptosis in Human Melanoma Cells," Mol. Cancer, 11(25), Apr. 2012, pp. 1-15.
Clarke et al., "Phase II Trial of Pemetrexed Disodium (ALIMTA, LY231514) in Chemotherapy-naïve Patients with Advanced Non-small-cell Lung Cancer," Ann Oncol., 13(5):737-741, May 2002.

(Continued)

*Primary Examiner* — Alexander R Pagano
(74) *Attorney, Agent, or Firm* — Haukaas Fortius PLLC; Michael H. Haukaas

(57) ABSTRACT

The invention provides a series of conformationally stable kinase inhibitors, and methods of using the kinase inhibitors. The effect of atropisomerism on kinase selectivity was assessed, finding improved selectivity compared to rapidly interconverting parent compounds.

12 Claims, 5 Drawing Sheets

(56) References Cited

OTHER PUBLICATIONS

Donato et al., "BCR-ABL Independence and LYN Kinase Overexpression in Chronic Myelogenous Leukemia Cells for Selected Resistance to STI571," Blood, 101(2):690-698, Jan. 2003.
Erdman et al., "Cancer Inflammation and Regulatory T Cells," Int J Cancer, 127(4):768-779, Aug. 2010.
Gabra et al., "Bcl-2 Inhibitor Scaffolds that are Preorganized Along an Axis of Chirality; the Effect of Atropisomerism on Protein Binding," San Diego State University, ProQuest Dissertations Publishing, Aug. 2015, pp. 1-72.
Gomez et al., "A Phase II Trial of Pemetrexed in Advanced Breast Cancer: Clinical Response and Association with Molecular Target Expression," Clin. Cancer Res., 12(3):832-838, Feb. 2006.
International Search Report and Written Opinion of the ISA/US dated Oct. 18, 2016 in International Application No. PCT/US2016/047085; 17pgs.
Laplante et al., "Assessing Atropisomer Axial Chirality in Drug Discovery and Development," J. Med. Chem., 54 (20):7005-7022, Aug. 2011.
Laplante et al., "Revealing Atropisomer Axial Chirality in Drug Discovery," ChemMedChem, 6(3):505-513, Mar. 2011.
Liu et al., "Structural Basis for Selective Inhibition of Src Family Kinases by PPI," Chem Biol., 6(9):671-678, Sep. 1999.
Maddox et al., "A Practical Lewis Base Catalyzed Electrophilic Chlorination of Arenes and Heterocycles," Org. Lett., 17(4):1042-1045, Feb. 2015.
Mulligan, "RET Revisited: Expanding the Oncogenic Portfolio," Nat Rev Cancer, 14(3):173-186, Mar. 2014.
Porter et al., "Tetrahydroisoquinoline Amide Substituted Phenyl Pyrazoles as Selective Bcl-2 Inhibitors," Bioorg Med Chem Lett., 19(1):230-233, Jan. 2009.
Tatton et al., "The Src-selective Kinase Inhibitor PP1 Also Inhibits Kit and Bcr-Abl Tyrosine Kinases," J Biol Chem., 278(7):4847-4853, Feb. 2003.
Widler et al., "7-Alkyl- and 7-Cycloalkyl-5-aryl-pyrrolo[2,3-d]pyrimidines—Potent Inhibitors of the Tyrosine Kinase c-Src," Bioorg Med Chem Lett., 11(6):849-852, Mar. 2001.
Xing et al., "Discovery and Characterization of Atropisomer PH-797804, a p38 MAP Kinase Inhibitor, as a Clinical Drug Candidate," ChemMedChem., 7(2):273-280, Feb. 2012.
Yoshida et al., "Synthesis, Resolution, and Biological Evaluation of Atropisomeric (aR)- and (aS)-16-Methyllamellarins N: Unique Effects of the Axial Chirality on the Selectivity of Protein Kinases Inhibition," J Med Chem., 56(18):7289-7301, Sep. 2003.
Zask et al., "Biological Stereoselectivity of Atropisomeric Natural Products and Drugs," Chirality. May 2013;25(5):265-74.

* cited by examiner

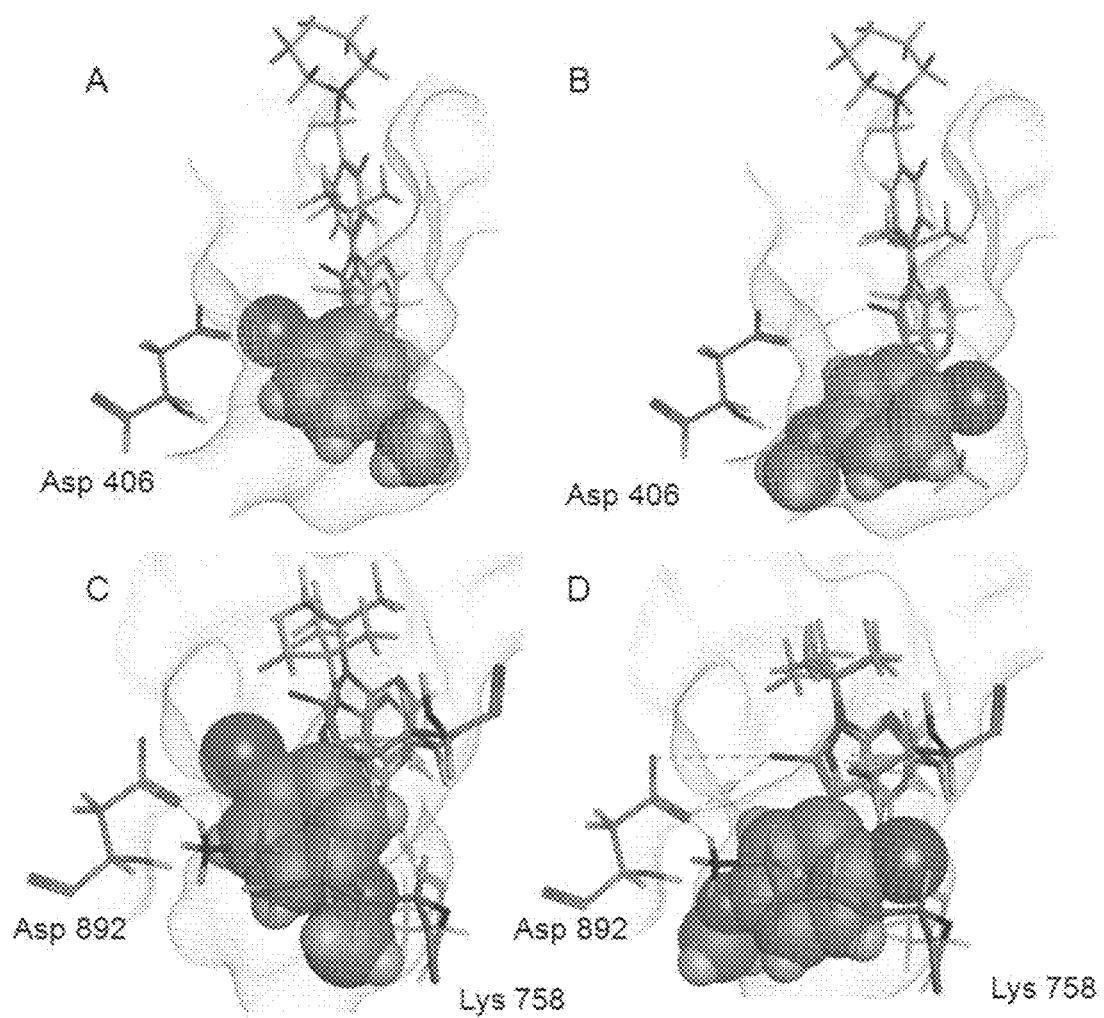
Fig. 4A-D

ATROPISOMERISM FOR INCREASED KINASE INHIBITOR SELECTIVITY

RELATED APPLICATIONS

This application is a National Stage filing under 35 U.S.C. § 371 of International Application No. PCT/US2016/047085 filed Aug. 15, 2016, which claims priority under 35 U.S.C. § 119(e) to U.S. Provisional Patent Application No. 62/204,735, filed Aug. 13, 2015, which applications are incorporated herein by reference.

BACKGROUND OF THE INVENTION

The human genome contains over 500 protein kinases. These kinases affect intracellular signal transduction pathways through protein phosphorylation. Aberrant kinase activity has been implicated in numerous diseases, leading to an intense drug discovery effort to develop efficacious anti-kinase therapeutics, resulting in over 20 FDA approved targeted kinase inhibitors mainly for the treatment of cancers including chronic myeloid leukemia and non-small cell lung cancer. While these efforts have revolutionized cancer therapy, a large degree of active site conservation throughout the kinase family causes most kinase inhibitors to possess promiscuous inhibition activities towards many kinases. While often needed for a complete response, this polypharmacology can also lead to side effects that negatively affect the quality of life, largely preventing kinase inhibitors from becoming therapeutics for chronic non-lethal diseases such as rheumatoid arthritis, where selectivity becomes a much larger requirement.

Kinase inhibitors are also common chemical probes to elucidate the role of a kinase or signaling pathways in cellular processes or disease. These fundamental studies are frequently confounded by off-target kinase inhibition affecting unintended signaling pathways. In recent years chemists and biologists have begun to gain an understanding of factors that can contribute to increasing the selectivity of a small molecule towards a specific kinase using 'selectivity filters' that take advantage of unusual features in a kinase active site, to obtain highly selective kinase inhibitors. A general selectivity filter has remained elusive as by design they rely on rare occurrences in an active site. Accordingly, a selectivity filter in kinase inhibition is needed in the art.

Atropisomerism is a form of chirality that arises from hindered rotation around an axis that renders the rotational isomers enantiomers. Many biologically active small molecules possess little hindrance to rotation and exist as a rapidly interconverting mixture of atropisomers, yet bind to their respective biological targets in an atropisomer specific manner. This dynamic nature of atropisomerism can cause serious complications in drug development, as atropisomers can display drastically different pharmacological profiles. This often results in confounding effects caused by the non-target relevant atropisomer, particularly when a compound possesses an intermediate stability, and can racemize over the length of the experiment.

Researchers have synthesized atropisomerically stable analogs of a lead molecule and have observed striking differential target affinities between the separated atropisomers (task et al., Chirality 2013, 25, 265-274; Porter et al., Bioorg. Med. Chem. Lett. 2009, 19, 1767-72), including a seminal report with a p38 MAP kinase inhibitor (Xing et al., ChemMedChem 2012, 7, 273-280). Atropisomerically pure analogs can also possess an improved toxicological profile since the non-target binding atropisomer is precluded. For example, Yoshida has recently synthesized atropisomeric lamellarin analogs, and found that each atropisomer possesses a notably different kinase inhibition profile with one atropisomer possessing improved selectivity compared to the parent molecule (Yoshida et al., J. Med. Chem. 2013, 56, 7289-7301). Accordingly, new atropisomers and methods for their preparation and evaluation are needed to provide improved kinase inhibitors with enhanced selectivity.

SUMMARY

The invention provides a method to study atropisomer conformation as a selectivity filter in kinase inhibition. The invention also provides compounds having increase kinase selectivity, and methods for increasing kinase selectivity. The invention therefore also provides atropisomers having increase kinase selectivity, for use in treating conditions that benefit from selective kinase inhibition.

Accordingly, the invention provides an atropisomer of a kinase inhibitor wherein the selectivity of the atropisomer is modulated compared to the corresponding rapidly interconverting parent kinase inhibitor, wherein the kinase inhibitor comprises an atropisomerism rotational blocking moiety on a rotatable moiety of the parent kinase inhibitor (e.g., a phenyl moiety), thereby providing the atropisomer having modulated kinase selectivity. In one embodiment, the atropisomer is an FDA approved kinase inhibitor comprising an atropisomerism rotational blocking moiety that substantially blocks rotation of a rotatable moiety thereby forming an atropisomer. In some embodiments, the atropisomer is a conformationally stable pyrrolopyrimidine.

In certain embodiments, the atropisomer is a kinase inhibitor of Formula I:

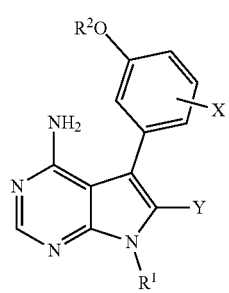

(I)

wherein
$R^1$ is $(C_1-C_8)$alkyl, $(C_3-C_8)$cycloalkyl, benzyl, or phenyl;
$R^2$ is H, $(C_1-C_4)$alkyl, or $(C_3-C_6)$cycloalkyl;
X is an atropisomerism rotational blocking moiety, wherein the blocking moiety is $(C_1-C_8)$alkyl, $(C_3-C_8)$cycloalkyl, or halo; and
Y is chloro, bromo, or methyl;
or salt or solvate thereof.

In some embodiments, the atropisomer of Formula I can be a kinase inhibitor of Formula X:

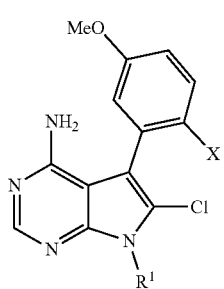

(X)

wherein

R$^1$ is cycloalkyl such as cyclopentyl, C$_3$-C$_8$)alkyl such as tert-butyl, or iso-pentyl or phenyl; and X is an atropisomerism rotational blocking moiety such as halo, cycloalkyl such as cyclopentyl, (C$_3$-C$_8$)alkyl such as tert-butyl, or iso-pentyl, or phenyl;

or salt or solvate thereof.

In one embodiment, X is chloro or bromo.

In certain specific embodiments, the atropisomer is 2e-(R) or 2e-(S):

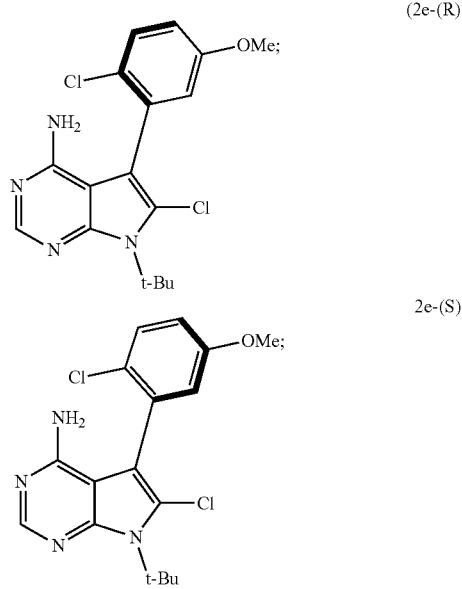

or a salt or solvate thereof.

The invention also provides a method to modulate the selectivity of atropisomeric kinase inhibitors comprising rigidifying an interconverting moiety of the kinase inhibitor to thereby provide one atropisomer having increase selectivity for one series of kinases and a second atropisomer having reduced selectivity for the series of kinases.

The invention further provides a method to modulate the selectivity of a promiscuous kinase inhibitor comprising adding an atropisomerism rotational blocking moiety to the inhibitor, thereby increasing or decreasing the selectivity of the kinase inhibitor.

The invention additionally provides novel compounds, intermediates for the synthesis of the compounds, as well as methods of preparing the compounds. The invention further provides compounds that are useful as intermediates for the synthesis of other useful compounds. The invention provides for the use of compounds for the manufacture of medicaments useful for the treatment of conditions that can be treated by kinase inhibitors.

Thus, the invention provides for the use of the compounds and compositions described herein for medical therapy. The medical therapy can be treating cancer, for example, breast cancer, lung cancer, such as non-small cell lung cancer, pancreatic cancer, prostate cancer, colon cancer, chronic myeloid leukemia, or thyroid cancer. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 4A-D. A and B) 2e-(S) (A) and 2e-(R) (13) docked to Src overlaid with electron density of CGP77675 in gold (PDB 1YOL), Interactions with Asp 406 represented by dashed lines. C and D) 2e-(S) (C) and 2e-(R) (D) docked to Ret overlaid with electron density of PPI (PDB: 2IVV). Interactions with Asp 892 and π-interactions with Lys 758 represented by dashed lines.

DETAILED DESCRIPTION

Figure 1A:
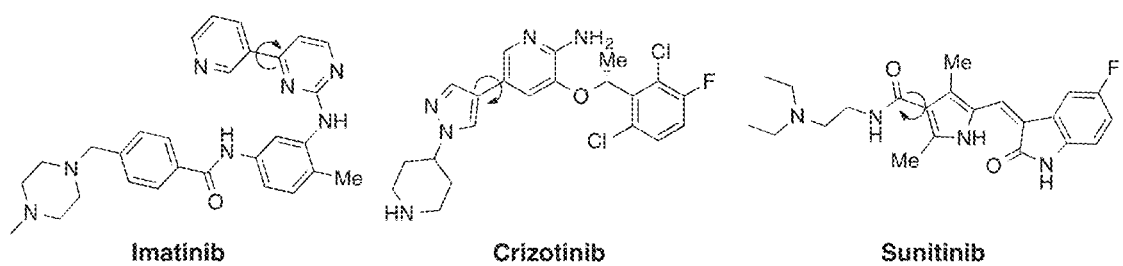
FIG. 1A-B. A) FDA approved kinase inhibitors that display interconverting atropisomerism. B) Some PPY and related kinase inhibitors.

Many biologically active molecules exist as rapidly interconverting atropisomeric mixtures. While one atropisomer inhibits the desired target, the other can lead to off-target effects. Herein we analyze atropisomerism as a tool to improve the selectivities of kinase inhibitors via the synthesis of conformationally stable pyrrolopyrimidines. Each atropisorner was isolated using chiral HPLC and subjected to inhibitor profiling across a panel of 18 tyrosine kinases. Notably different selectivity patterns between atropisomers were observed, as well as improved selectivity compared to a rapidly interconverting parent molecule. Computational docking studies then provided insights on the structural-based origins of these effects. This study is one of the first examples of the intentional preorganization of a promiscuous scaffold along an atropisomeric axis to increase target selectivity, and provides fundamental insights that may be applied to other atropisomeric target scaffolds.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's *Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," will be understood that the particular value without the modifier "about" also forms a further aspect.

The term "about" can refer to a variation of ±5%, ±10%, ±20%, or ±25 of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition or embodiment. The term about can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "alkyl" refers to a branched or unbranched hydrocarbon having, for example, from 1-20 carbon atoms, and often 1-12, 1-10, 1-8, 1-6, or 1-4 carbon atoms, Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl 2 butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups when specifically noted. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 or from 3 to 8 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-en cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "halo" or "halide" refers to fluoro, chloro, bromo, or iodo. Similarly, the term "halogen" refers to fluorine, chlorine, bromine, and iodine.

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replaced by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl (e.g., vinyl, or allyl), alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure; or combinations thereof. Additionally, suitable substituent groups can be, e.g., —X, —R, —O$^-$, —OR, —SR, —S$^-$, —NR$_2$, —NR$_3$, —N=NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, cycloalkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more substituents above can be excluded from the group of potential values for substituents on the substituted group. The various R groups in the schemes and figures of this disclosure can be one or more of the substituents recited above, thus the listing of certain variables for such R groups (including R$^1$, R$^2$, R$^3$, etc.) are representative and not exhaustive, and can be supplemented with and/or substituted by one or more of the substituents above.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, preventing, lowering, stopping or reversing the progression or severity of the condition or symptoms being treated. As such, the term "treatment" can include medical, therapeutic, and/or prophylactic administration, as appropriate.

The term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art. The cancer cells can result in the formation of a tumor. The term "tumor" refers to a neoplasm, typically a mass that includes a plurality of aggregated malignant cells. Cancer of varying types (e.g., those recited herein) and the resulting tumors can be treated by the atropisomers described herein.

The terms "inhibit", "inhibiting" and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "atropisomers" refers to conformational stereoisomers that occur when rotation about a single bond in the molecule is prevented, or greatly inhibited, as a result of steric interactions with other parts of the molecule and the substituents at both ends of the single bond are asymmetrical, i.e., optical activity arises without requiring an asymmetric carbon center or stereo center. Where the rotational barrier about the single bond is high enough, and interconversion between conformations is slow enough, separation and isolation of the isomeric species is often achievable by standard separation techniques such as HPLC. Atropisomers are enantiomers without requiring a single asymmetric atom. Atropisomers are considered stable if the barrier to interconversion is high enough to permit the atropisomers to undergo little or no interconversion at room temperature for at least a week, preferably at least a year. In some embodiments, an atropisomeric compound as described herein does not undergo more than about 5% interconversion to its opposite atropisomer at room temperature during one week when the atropisomeric compound is in substantially pure form, which is generally a solid state. In some embodiments, an atropisomeric compound does not undergo more than about 5% interconversion to its opposite atropisomer at room temperature (approximately 25° C.) during one year. Preferably, the atropisomeric compounds are stable enough to undergo no more than about 5% interconversion in an aqueous pharmaceutical formulation held at 0° C. for at least one week.

The energy barrier to thermal racemization of atropisomers can be determined by the steric hindrance to free rotation of a bonds forming a chiral axis. Some biaryl compounds exhibit atropisomerism where rotation around an interannular bond lacking C2 symmetry is restricted. The free energy barrier for isomerization (enantiomerization) is a measure of stability of the interannular bond with respect to rotation. Optical and/or thermal excitation can promote racemization of such isomers, dependent on electronic and steric factors.

The term "conformationally stable atropisomer" refers to an atropisomer that is conformationally stable such that it has a barrier to rotation of at least about 25 kcal/mol, at least about 26 kcal/mol, or at least about 27 kcal/mol. The stability of a conformationally stable atropisomer is such that its $t_{1/2}$ at 37° C. is at least about 8 days, at least about 10 days, at least about 12 days, at least about 15 days, at least about 18 days, at least about 150 days, or at least about 300 days. A conformationally stable atropisomer is thus a stereochemically stable at room temperature.

The term "atropisomerism rotational blocking moiety" is a group that, when covalently bonded to a rotatable phenyl moiety of a kinase inhibitor, increases the barrier to rotation of the phenyl moiety such that the molecule becomes an atropisomer that is conformationally stable, as described above.

Embodiments of the Invention

The invention provides a conformationally stable atropisomer of a pyrrolopyrimidine-based kinase inhibitor wherein the selectivity of the atropisomer is modulated compared to the corresponding rapidly interconverting parent kinase inhibitor, wherein the pyrrolopyrimidine-based kinase inhibitor comprises an atropisomerism rotational blocking moiety on a rotatable phenyl moiety of the parent kinase inhibitor that conformationally stabilizes the atropisomer having modulated kinase selectivity. The atropisomer can have an at least a 3-fold increase in selectivity toward a specific kinase compared to the corresponding kinase inhibitor lacking the atropisomerism rotational blocking moiety.

The invention thus provides an atropisomer wherein the atropisomer is a kinase inhibitor of Formula I:

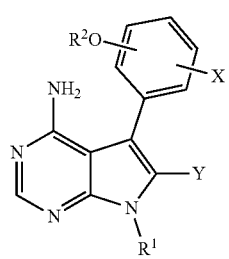

(I)

wherein
R$^1$ is (C$_1$-C$_8$)alkyl, (C$_3$-C$_8$)cycloalkyl, benzyl, or phenyl;
R$^2$ is H, (C$_1$-C$_4$)alkyl, or (C$_3$-C$_6$)cycloalkyl;
X is an atropisomerism rotational blocking moiety, wherein the blocking moiety is (C$_1$-C$_8$)alkyl, (C$_3$-C$_8$) cycloalkyl, or halo; and
Y is chloro, bromo, or methyl;
or salt or solvate thereof. Preferably the group OR$^2$ is located meta to the bond connecting its phenyl group to the pyrrolopyrimidine moiety of the molecule. Accordingly, the kinase inhibitor of Formula I can be a kinase inhibitor of Formula II:

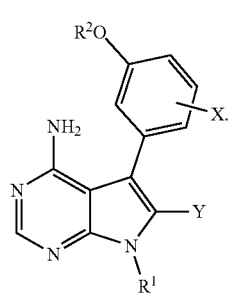

(II)

The group X can be ortho, meta, or para to the group OR$^2$. Preferably, the group X is meta or para to the group OR$^2$. In some embodiments, X is meta to the group OR$^2$. In other embodiments, X is para to the group OR$^2$.

In some embodiments, R$^1$ is methyl, cyclopentyl, tert-butyl, iso-pentyl, or phenyl. In one specific embodiment, R$^1$ is iso-propyl. In another specific embodiment, R$^1$ is tert-butyl. In another specific embodiment, R$^1$ is iso-pentyl.

In some embodiments, R$^2$ is H. In other embodiments, R$^2$ is Me. In yet other embodiments, R$^2$ is Et.

In some embodiments, X is chloro, bromo, or methyl. In one specific embodiment, X is chloro. In another specific embodiment, X is bromo. In another specific embodiment, X is methyl.

In some embodiments, Y is chloro, bromo, or methyl. In one specific embodiment, Y is chloro. In another specific embodiment, Y is bromo. In another specific embodiment, Y is methyl.

In other embodiments, the atropisomer of Formula I is a kinase inhibitor of Formula X:

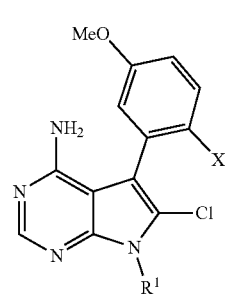

(X)

wherein
R$^2$ is cyclopentyl, tert-butyl, iso-pentyl, or phenyl; and
X is an atropisomerism rotational blocking moiety, wherein the blocking moiety is methyl, halo or (C$_3$-C$_8$) cycloalkyl;
or salt or solvate thereof.
In certain embodiments, X is chloro or bromo.
In various specific embodiments, the atropisomer of Formula I or Formula X is:

2e-(R) 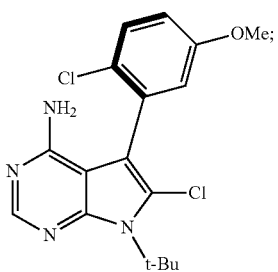

2e-(S) 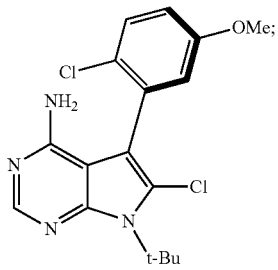

2f-(R) 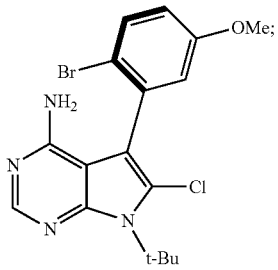

2f-(S) 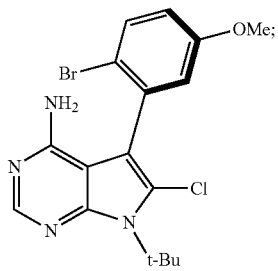

2m-(R) 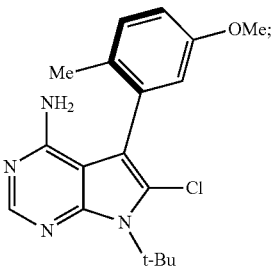

2m-(S) 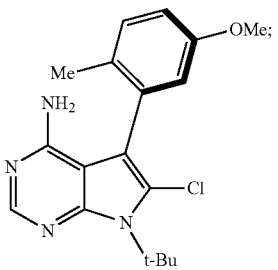

or a salt or solvate thereof. The invention also provides various embodiments where the groups X and OR$^2$ on the phenyl ring are meta or para to each other, wherein one of the groups X and OR$^2$ is ortho to the bond connecting its phenyl group to the pyrrolopyrimidine moiety of the molecule.

The invention also provides a pharmaceutical composition comprising an atropisomer described herein (e.g., an atropisomer of Formula I, Formula II, or Formula X) in combination with a pharmaceutically acceptable diluent, carrier, or excipient. The composition can consist of only one atropisomer. For example, the composition can include an atropisomer that is at least about 95% or at least about 99% in the (R) configuration, or at least about 95% or at least about 99% in the (S) configuration.

The invention further provides a method of inhibiting the growth of cancer cells comprising administering to a mammal having cancer a therapeutically effective amount of an atropisomer described herein, thereby inhibiting the growth of cancer cells in the mammal.

In one embodiment, the atropisomer is the (R)-atropisomer and the atropisomer is selective for RET kinase, YES kinase, or a combination thereof. The cancer cells can be cancer cells that cause Gastrointestinal Stromal Tumors (GIST), medullary thyroid cancer, ER-positive breast cancer, or non-small cell lung cancer. In other embodiments, the cancer cells can be cancer cells that cause melanoma, breast cancer, or rhabdomyosarcoma.

In another embodiment, the atropisomer is the (S)-atropisomer and the atropisomer is selective for SRC kinase, ABL kinase, YES kinase, or a combination thereof. The cancer cells can be cancer cells that cause breast cancer, colon cancer, or prostate cancer. In other embodiments, the cancer cells can be cancer cells that cause Chronic Myeloid Leukemia. In yet another embodiment, the cancer cells can be cancer cells that cause melanoma, breast cancer, or rhabdomyosarcoma.

Thus, the invention provides a method of treating cancer in a mammal comprising administering to a mammal having cancer a therapeutically effective amount of an atropisomer described herein, thereby treating the cancer in the mammal. The cancer can be, for example, one of the cancers described herein, wherein the kinase inhibitor is selective for a kinase that promotes or exacerbates the growth or stability of the cancer cells.

Additionally, the invention provides a method to modulate the selectivity of a promiscuous kinase inhibitor that comprises a rotatable phenyl moiety comprising adding an atropisomerism rotational blocking moiety to the phenyl moiety of the inhibitor, thereby increasing or decreasing the selectivity of the kinase inhibitor for specific kinases. The kinase inhibitor can be, for example, a pyrrolopyrimidine-based kinase inhibitor, for example, a kinase inhibitor as described herein.

Atropisomeric Compounds and Selectivity

Figure 1B:
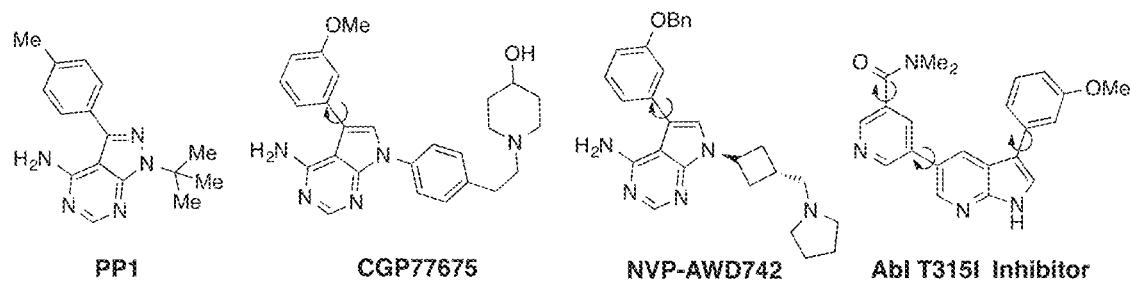

As rapidly interconverting atropisomerism is ubiquitous throughout kinase inhibitors (FIG. 1A), we set out to evaluate atropisomerism as a strategy to improve the selectivity of promiscuous kinase inhibitors. For these initial studies we chose pyrrolopyrimidine-based kinase inhibitors (PPYs) because they represent a common and promiscuous kinase inhibitor scaffold that often possess at least one atropisomeric axis (FIG. 1B). Furthermore, the identification of PPY analogs having improved kinase selectivity may provide intriguing starting points for drug discovery, and toward valuable chemical probes for the investigation of kinase signaling pathways. Fundamentally, PPYs represent an enticing but challenging platform for this work, as while crystallographic analysis (i.e. PDB: 1YOL) suggests they can bind kinases in atropisomer specific manners, PPYs rely primarily on conserved interactions between the kinase active site and the 'adenine like' heterocycle for potency.

We developed a simple synthesis of atropisomerically rigidified PPY analogs (Scheme 1) starting from readily available N-alkylated pyrrolopyrimidines. The choice of N-substitution was based on previous work on PPYs (Altmann et al., *Bioorg. Med. Chem. Lett.* 2001, 11, 849-852) and related (i.e. PP1) kinase inhibitors (Liu et al., *Chem. Biol.* 1999, 6, 671-8). Our recently disclosed phosphine sulfide catalyzed halogenation (Maddox, Nalbandian, Smith, and Gustafson, *Org. Lett* 2015, 17, 1042-1045) proved crucial throughout this synthesis as it facilitated iodination of the PPY core (to give 1b and 2b), boronic acid halogenation (to give 3 and 4), and the key late stage chlorination of the PPY core to rigidify the axis in the penultimate step. Nucleophilic aromatic substitution of the 6-Cl with ammonia led to racemic PPY analogs (1e, 1f, 2e, 2f).

Scheme 1. Synthesis of atropisomerically stable PPY kinase inhibitors.

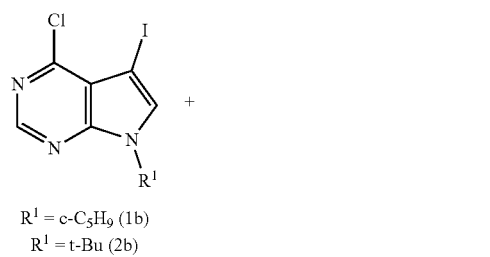

$R^1$ = c-$C_5H_9$ (1b)
$R^1$ = t-Bu (2b)

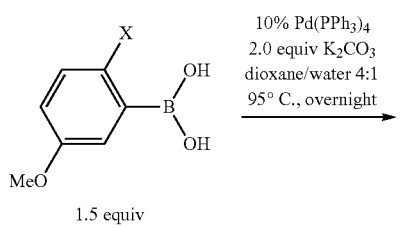

1.5 equiv

X = Cl (3)
X = Br (4)

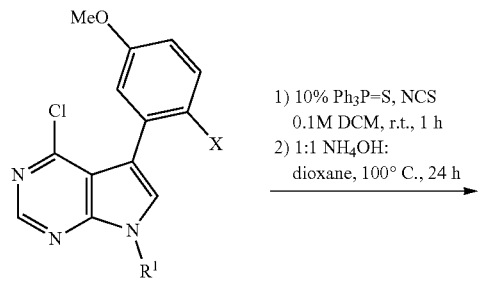

$R^1$ = c-$C_5H_9$, X = Cl (1c)
$R^1$ = c-$C_5H_9$, X = Br (1d)
$R^1$ = t-Bu, X = Cl (2c)
$R^1$ = t-Bu, X = Cl (2d)

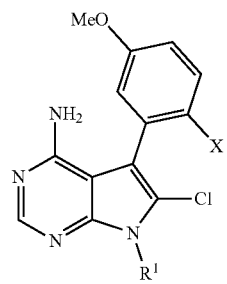

$R^1$ = c-$C_5H_9$, X = Cl (1e)
$R^1$ = c-$C_5H_9$, X = Br (1f)
$R^1$ = t-Bu, X = Cl (2e)
$R^1$ = t-Bu, X = Br (2f)

Figure 2A:
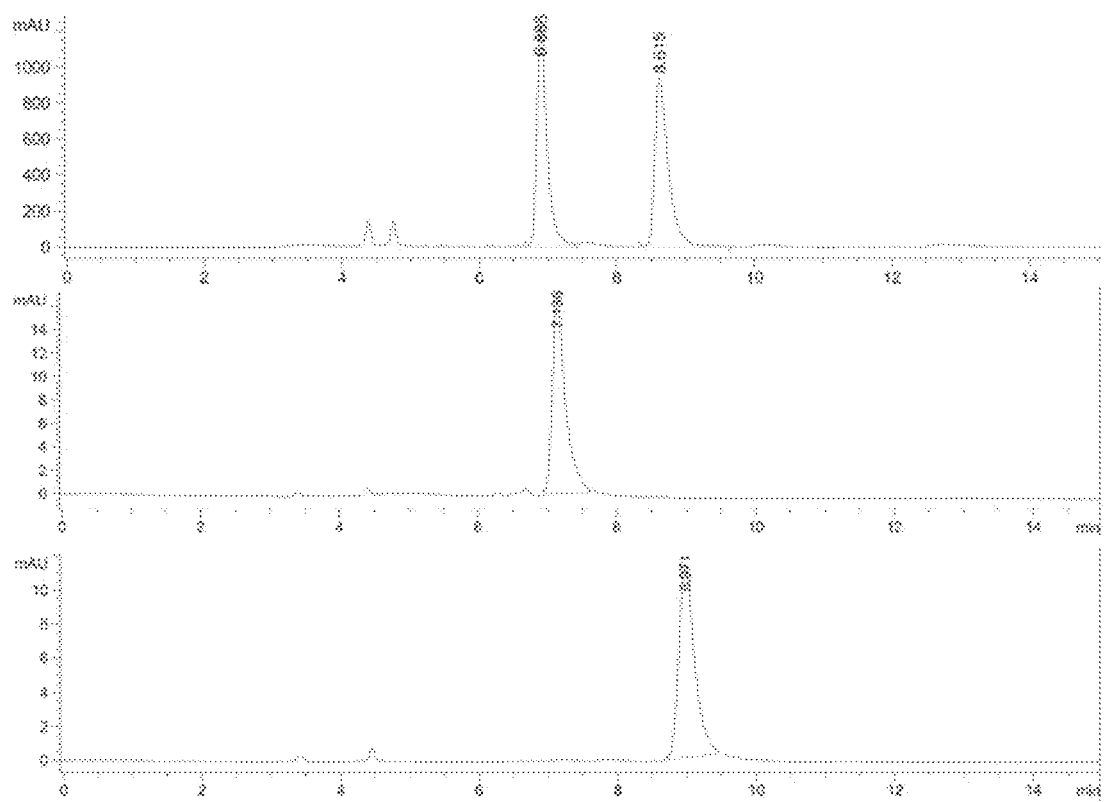
FIG. 2A-C. A) Chiral HPLC traces of 2e before and after separation of atropisomers. B) Circular dichroism spectra of separated atropisomers of 2e. C) X-Ray crystal structure of first eluting atropisomer of 1f ((R) configuration). The supplementary crystallographic data for (1f-(12)) has been submitted to the Cambridge Crystallographic Data Centre (CCDC). These data can be obtained free of charge from the CCDC via CCDC.Cam.ac.uk/data_request/cif.
Figure 2B:
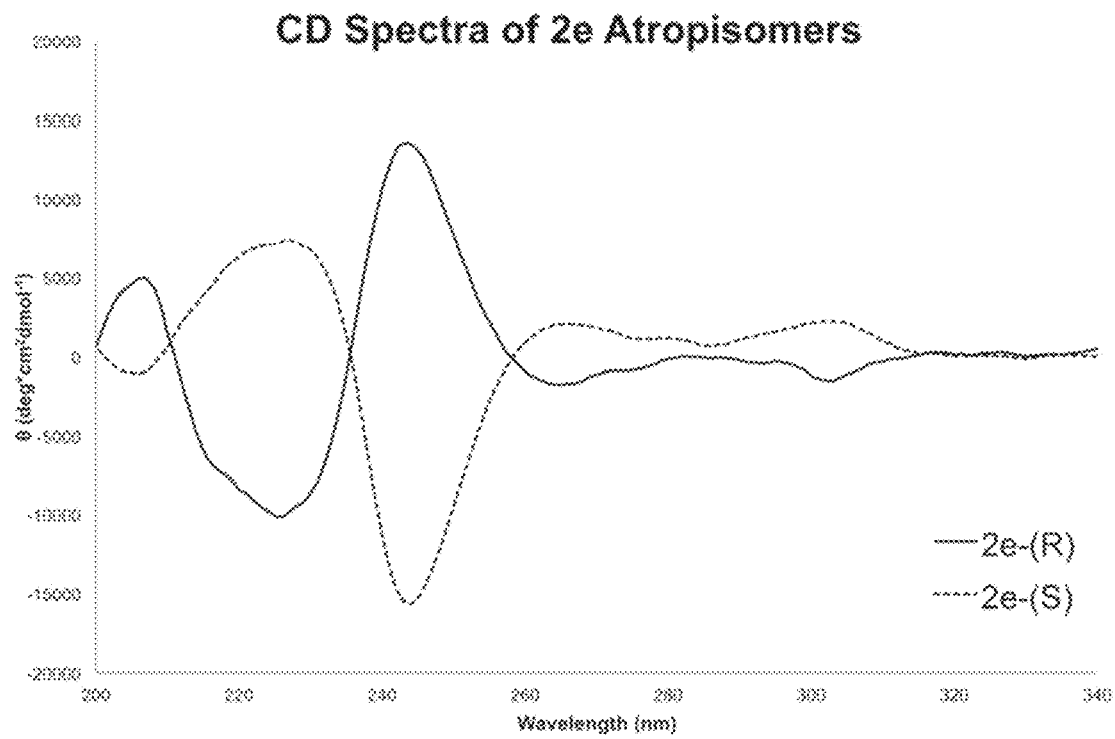
Figure 2C:
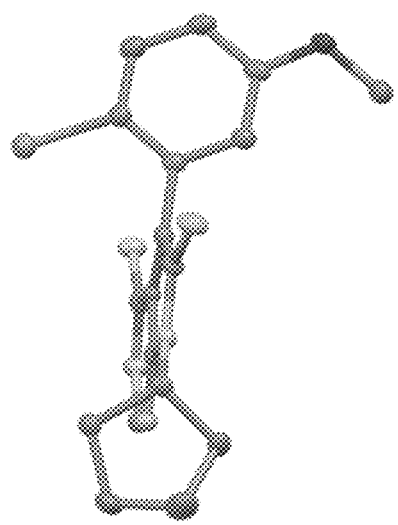

Chlorine substitution proved sufficiently large to render the axis stereochemically stable at room temperature, and each atropisomer was obtained using chiral semi-preparative HPLC (FIG. 2A). A sufficiently large blocking group such as chlorine is referred to herein as an atropisomerism rotational blocking moiety. Circular dichroism confirmed that the isolated peaks were indeed enantiomeric atropisomers (FIG. 2B), and X-ray crystallography revealed that the first eluting atropisomer of 1f was in the (R) configuration (FIG. 2C). As each series is structurally similar, and were separated using comparable HPLC conditions, we assigned the conformations of 1e, 2e and 2f by analogy.

We then experimentally measured the barrier to rotations of each series via HPLC (Barrett et al., *Nature* 2014, 509, 71-75) observing stereochemical stabilities ranging from 8 days to 8 years at physiological temperature. Interestingly, we found that the steric size of the N-substitution ($R^1$) distal to the axis had a clear effect on the barrier to rotation, with tert-butyl substitution increasing the barrier to rotation by 1.2-1.5 kcal/mol over cyclopentyl substitution, resulting in a change in stereochemical stability at 37° from 18 days for 1e to 157 days for 2e (Scheme 2). This trend is a manifestation of 'the buttress effect' (Bringmann et al., *Anger. Chemie Int. Ed.* 2005, 44, 5384-5427) and represents a strategy to increase stereochemical stabilities when needed.

Scheme 2. Experimentally measured barriers to rotation, and extrapolated $t_{1/2}$ to racemization at 37° C.

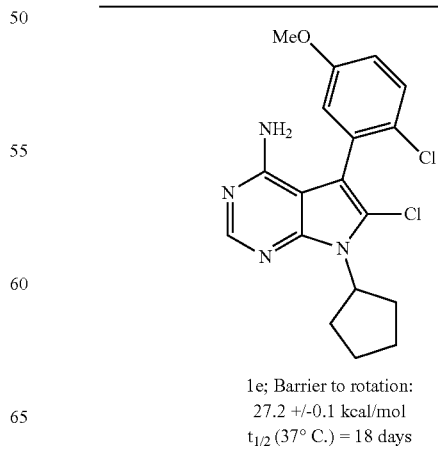

1e; Barrier to rotation:
27.2 +/-0.1 kcal/mol
$t_{1/2}$ (37° C.) = 18 days

-continued

1f; Barrier to rotation:
29.0 +/-0.06 kcal/mol
$t_{1/2}$ (37° C.) = 301 days

2e; Barrier to rotation:
28.6 +/-0.06 kcal/mol
$t_{1/2}$ (37° C.) = 157 days

2f; Barrier to rotation:
30.4 +/-0.06 kcal/mol
$t_{1/2}$ (37° C.) = 8 Years

Based on the observed stereochemical stabilities, we chose 1f, 2e, and 2f for further study and obtained inhibition data against Src kinase from Life Technologies' Z'-LYTE™ kinase assay (Scheme 3). While the atropisomeric analogs were roughly 7-14 times less potent than a non-rigidified 'parent' molecule 5, the atropisomers displayed striking differential potencies. For example, while the second eluting (5) atropisomer of 1f possessed an $IC_{50}$ of 1,300 nM, the first eluting (R) atropisomer displayed significantly less potency with an $IC_{50}$ of greater than 10,000 nM. The trend of the first eluting atropisomer possessing attenuated Src inhibitory activity compared to the $2^{nd}$ eluting peak held throughout each series tested, lending further credence to the conformational assignment based on the X-ray crystal structure of 1f.

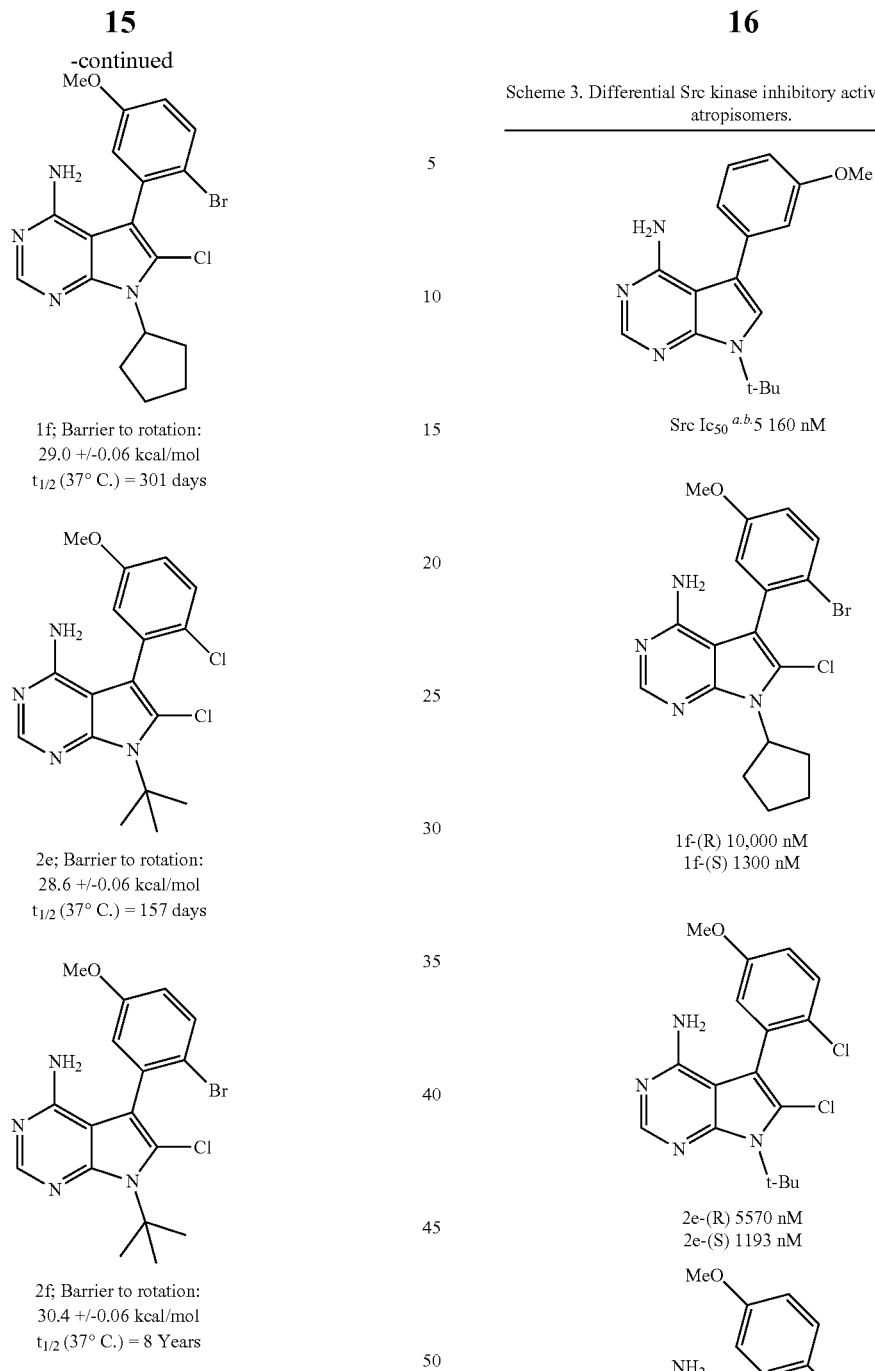

Scheme 3. Differential Src kinase inhibitory activities between atropisomers.

Src $Ic_{50}$ [a,b] 5 160 nM 1f-(R) 10,000 nM
1f-(S) 1300 nM 2e-(R) 5570 nM
2e-(S) 1193 nM 2f-(R) 3780 nM
2f-(S) 2320 nM

[a] Data obtained at Life Technologies using the Z'-LYTE kinase inhibtion platform.
[b] Data is the average of 2 runs.

In order to probe the effect of atropisomeric conformation on kinase selectivity we subjected 1f, 2e, and 2f to kinase inhibitor profiling across a panel of tyrosine kinases at 1000 nM and 5000 nM (data for 2e shown in Scheme 4 below).

Scheme 4. Percent inhibition of 2e atropisomers and 'parent' compound 5 across a panel of tyrosine kinases at 2 concentrations.

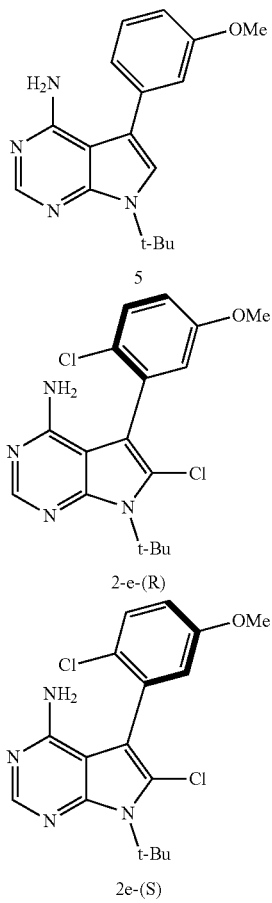

somer provides at least 50% inhibition, at least 70% inhibition, or at least 80% inhibition. The invention also provides selective kinase inhibitors wherein an (S)-atropisomer is selective for a kinase of Scheme 4 and provides at least 20%, at least 30%, or at least 35% greater selectivity for the kinase compared to the (R)-atropisomer, at a particular concentration, or vice versa.

The majority of kinases in the panel preferred the (S-atropisomer to varying degrees, however comparing the kinase inhibition profile of each atropisomer revealed some fascinating differential selectivities. For example, the (R)-atropisomer of 2e was less active towards Src than the (S)-atropisomer, yet it inhibited Ret kinase, a validated drug target for numerous cancers including medullary thyroid cancer, to a significantly greater degree than the (S)-atropisomer (73% vs 32% at 5000 nM, Scheme 4). Conversely, the (S)-atropisomer inhibited Abl kinase to a significantly greater degree than the (R)-atropisomer (67 vs 26% at 5000 nM, Scheme 4).

We also performed the profiling experiment with the more potent 'parent' molecule 5, albeit at lower concentrations to account for its increased potency (200 nM and 1000 nM), finding 5 possessed near pan activity for the tyrosine kinase panel tested, including significant activity toward kinases Src, Ret and Abl.

To analyze each analog's selectivity across the panel we turned to selectivity scores (Davis et al., *Nat. Biotechnol.* 2011, 29, 1046-51), simply the number of kinases inhibited above a certain threshold divided by the number of kinases evaluated. In general the (R)-atropisomer was more selective, inhibiting a lower percentage of kinases tested to an intermediate degree (defined as greater than 40% inhibition). For example at 1000 nM 2e-(R) yielded an S(40%) of 0.11 while 2e-(S) gave an S(40%) of 0.16. The parent molecule 5 was less selective at a lower concentration of 200 nM giving an S(40%) value of 0.44 (see Scheme 4). Differences in selectivity between 2e-(R) and 2e-(S) at 5000 nM (4.5 times the $IC_{50}$ of 2e-(S) toward Src) and for 5 at 1000 nM (6.25 times the $IC_{50}$ of 5 toward Src) can be viewed

| Kinase[a] | % inhibition 200 nM[b] | % inhibition 1000 nM[b] | % inhibition 1000 nM[b] | % inhibition 5000 nM[b] | % inhibition 1000 nM[b] | % inhibition 5000 nM[b] | SIR (5000 nM)[d] |
|---|---|---|---|---|---|---|---|
| Abl | 37% | 78% | 11% | 26% | 36% | 67% | 2.57 |
| Alk | 11% | 23% | 6% | 18% | 5% | 7% | 0.38 |
| Blk | 38% | 74% | 3% | 32% | 21% | 47% | 1.46 |
| BTK | 62% | 90% | 10% | 29% | 18% | 54% | 1.86 |
| CSK | 36% | 65% | 21% | 35% | 19% | 45% | 1.28 |
| EGFR | 28% | 62% | −4% | 0% | 10% | 21% | — |
| Her-2 | 4% | 16% | −2% | 0% | −7% | 0% | — |
| Fgr | 69% | 92% | 45% | 77% | 58% | 81% | 1.05 |
| Fyn | 56% | 84% | 19% | 44% | 26% | 56% | 1.27 |
| Hck | 59% | 80% | 24% | 40% | 32% | 50% | 1.25 |
| Kit | 8% | 27% | 5% | 26% | 18% | 36% | 1.38 |
| Lck | 32% | 79% | 23% | 51% | 26% | 54% | 1.05 |
| Lyn | 58% | 85% | 19% | 57% | 36% | 75% | 1.31 |
| pdgfr-a | 11% | 34% | 3% | 8% | 3% | 13% | 1.63 |
| pdgfr-b | 6% | 19% | 4% | 13% | 13% | 16% | 1.23 |
| Ret | 59% | 89% | 35% | 73% | 14% | 32% | 0.44 |
| Yes | 63% | 90% | 53% | 79% | 53% | 77% | 0.97 |
| S(40%)[c] | 0.44 | 0.72 | 0.11 | 0.44 | 0.16 | 0.61 | — |

[a]Data obtained at Life Technologies using the Z'-LYTE kinase inhibition platform.
[b]Data is the average of 2 runs.
[c]Number of kinases inhibited greater than 40% divided by number of kinases tested (including Src).
[d]% inhibition 2e-(S)/% inhibition 2e-(R).

Figure 3:
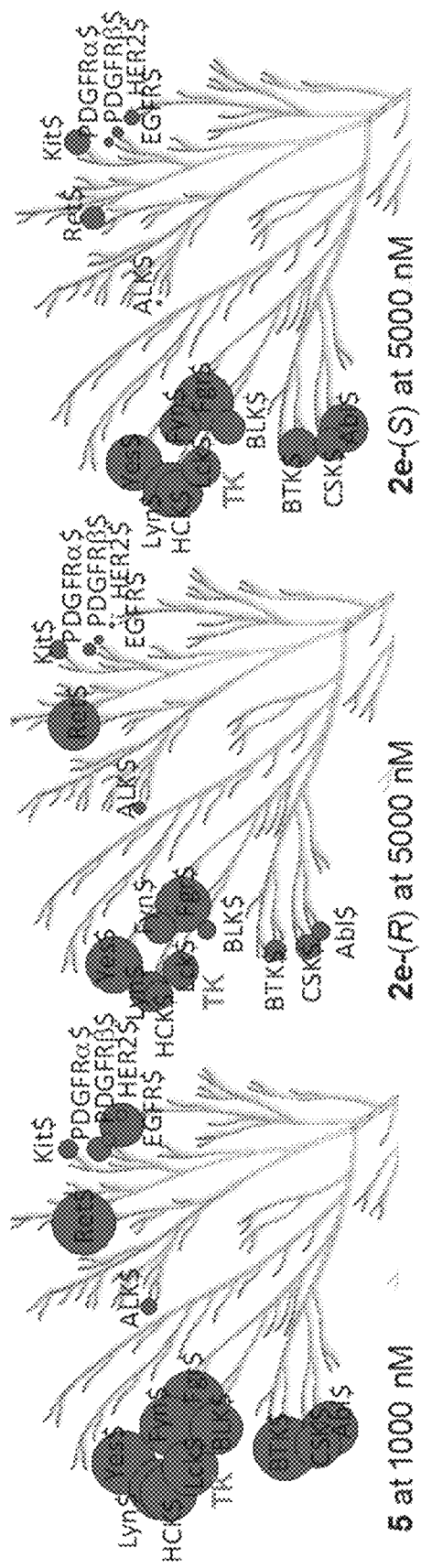
FIG. 3. The tyrosine kinase branch of the kinome annotated with red circles, scaled to percent inhibition. Illustrations reproduced courtesy of Celt Signaling Technology, Inc. (cellsignal.com).

Thus, the invention provides selective kinase inhibitors wherein an (S)-atropisomer or (R)-atropisomer is selective for a kinase of Scheme 4, for example, wherein the atropisomer provides at least 50% inhibition, at least 70% inhibition, or at least 80% inhibition. The invention also provides selective kinase inhibitors wherein an (S)-atropisomer graphically across tyrosine kinases (FIG. 3). Importantly, similar trends were also observed across each of the atropisomeric series tested.

We then obtained $IC_{50}$ data of 5 and the 2e series toward a subset of kinases that displayed differential atropisomeric activities (Src, EGFR, Ret, Ahl, YES (Table 1)). This data validated the profiling results, and also helped quantitate differential selectivity between atropisomers.

observed data and structural assignment. Likewise this experiment predicted that EGFR would bind both atropisomeric conformations with very little difference in the docking scores. Together these experiments illustrate that the existence of an inherent atropisomer preference can be

TABLE 1

$IC_{50}$ data of atropisomeric kinase inhibitors.

| Kinase | 5 IC50 | IC50 of 5 Kinase/ IC50 of 5 Yes | 2e-(R) IC50 | IC50 of 2e-(R) Kinase/ IC50 of 2e-(R) Yes | 2e-(S) IC50 | IC50 of 2e-(S) Kinase/ IC50 of 2e-(S) Yes |
|---|---|---|---|---|---|---|
| Src | 151 +/− 9 nM[b] | 1.64 | 5570 +/− 907 nM[b] | 6.22 | 1193 +/− 170 nM[b] | 1.64 |
| EGFR | 641 +/− 54 nM[b] | 6.96 | >10,000 nM[c] | >10.0 | >10,000 nM[c] | >10.0 |
| Yes | 92 +/− 11 nM[b] | 1 | 895 +/− 90 nM[b] | 1 | 727 +/− 177 nM[b] | 1 |
| Ret | 128 +/− 3 nM[b] | 1.4 | 1857 +/482 nM[b] | 2.07 | 7659 +/− 754 nM[b] | 10.53 |
| Abl | 244.5 +/− 19 nM[c] | 2.65 | >10,000 nM[c] | 10.0 | 1432 +/− 210 nM[c] | 1.96 |

[a]Data obtained at Life Technologies using the Z'-LYTE kinase inhibition platform. Error is Standard Deviation.
[b]IC50 determined in triplicate.
[c]IC50 determined in duplicate.

Parent molecule 5 displayed little selectivity toward the kinases tested with 1.4-2.65 fold relative selectivities favoring Yes (IC50 kinase/IC50 YES) over Ret, Src, and Abl, and a 7 fold selectivity between YES and EGER. As with the profiling data the atropisomeric analogs possessed enhanced selectivities compared to 5. For example, 2e-(R) inhibited Ret kinase with an $IC_{50}$ of 1857 nM, but possessed reduced potency towards Ahl and Src (10,000 nM, and 5570 nM), representing a 4-fold augmentation of 5's inherent selectivity towards these kinases. Conversely, the (S) configuration was less potent towards Ret (7659 nM, a nearly 8 fold increase of 5's inherent selectivity), while maintaining activity towards Src and Abl (1193 nM, and 1432 nM). In general, this data demonstrates that different members of highly conserved families of enzymes such as kinases can prefer different atropisomer conformations of the same inhibitor, and that this can be harnessed to modulate inhibitor promiscuity. Some kinases in these profiling experiments did not display differential selectivities between atropisomers. For example, EGFR activity was knocked out across both atropisomers while other kinases (Fgr, Yes) maintained comparable activity towards each atropisomer, suggesting that the atropisomeric conformation does not significantly influence binding in certain specific kinases.

To gain a better understanding of the physical basis of the observed effects we turned to molecular modeling. We docked 5 into known structures of Ret, Src and EGFR bound to ligands that were structurally similar to PPYs. This experiment predicted that Ret and Src would bind 5 in different atropisomeric conformations that agreed with the predicted. In silico, representing a tool that allows for rapid assessment of the utility of applying this approach to a particular kinase target.

We also examined each atropisomer of 2e. In Src, the 2e-(S) atropisomer is predicted to fit in the binding site (FIG. 4A) and contribute stabilizing interactions with neighboring Asp 406. The binding mode of 2e-(S) is consistent with that of CGP77675 (PDB 1YOL) making the same pyrrolopyrimidine hydrogen bonds and having similar dihedral angles between the two aryl ring systems, 57.25° vs 54.56°. The docked poses also suggest that the preference for 2e-(S) may arise from slight steric clashes between the methoxy group on 2e-(R) (FIG. 4B) with surrounding residues that are not near it in 2e-(S).

In Ret, the active atropisomer 2e-(R) has a binding mode similar to that of PPI (PDB 2IVV) making the same pyrrolopyrimidine hydrogen bonds and having similar dihedral angles between the two aryl ring systems, −122.57° vs −116.87° (FIG. 4D) and is predicted to possess stabilizing interactions with Asp 892 as well as π-interactions with neighboring Lys 758 that are not present with 2e-(S) (FIG. 4C). Additionally, 2e-(S) is predicted to have a steric clash between chlorine and Asp 892 that causes the docked pose to shift up with regards to the X-ray configuration, straining the hydrogen bonds between the pyrrolopyrimidine ring and the neighboring Glu 805 and Ala 807 residues. All these factors indicate physico-chemical origins for the observed 2e-(R) selectivity towards Ret.

A close examination of the bound 5-(S) and 5-(R) poses in the EGFR binding pocket do not predict any additional protein-ligand interactions other than the two pyrrolopyrimidine hydrogen bonds similar to the ones made by ATP. Both atropisomers seem to fit well in the binding site without apparent steric clashes. In contrast, there seem to be significant steric clashes between the 2e-(S) methoxy group as well as the 2e-(R) chlorine with the neighboring residues in the ATP binding site. This is consistent with the observed loss of activity. Interestingly, docking studies performed with the inactive form of EGFR (PDB 2GS7) resulted in a very clear preference for 2e-(S). This will be explored in future studies.

Taken together our data indicate that atropisomerism can be leveraged to modulate the selectivity of promiscuous kinase inhibitors. While some of the observed changes in selectivity between 5 and each atropisomer of 2e may be due to the decreased potency of the analogs, we feel that the differences in kinase profile in Table 1 among atropisomers, as well as the increased selectivities of 2e (R) and at higher concentrations to that of 5 suggest that many of the observed difference are due to differential protein recognition towards atropisomers.

To the best of our knowledge this work represents one of the first examples of the strategic rigidification of a common and promiscuous medicinal chemical scaffold around an axis of chirality to improve upon target selectivity. The presented data illustrates fundamentally that in many cases control of atropisomeric conformation can be leveraged as a general strategy to improve the selectivity profile of kinase inhibitors. While the observed effects on selectivity may be modest compared to covalent strategies, covalent approaches inherently rely on relatively rare occurrences in the kinase active site limiting their implementation. On the other hand, the ubiquity of atropisomerism in drug discovery should present ample opportunities for it to be applied as a more general approach, often as part of a larger medicinal chemical puzzle, to obtain more selective kinase inhibitors.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5th Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will he 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip, L; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will he dependent upon the chemistry of the reaction to be protected against (e.g., acidic, basic, oxidative, reductive or other conditions) and the intended direction of the synthesis.

Pharmaceutical Formulations

The compounds described herein can be used to prepare therapeutic pharmaceutical compositions, for example, by combining the compounds with a pharmaceutically acceptable diluent, excipient, or carrier. The compounds can be a single atropisomer, such as the atropisomers described herein. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained, using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can he maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Compound Preparation and Characterization $^1$H and $^{13}$C NMR spectra were recorded on Varian VNMRS 400 MHz, and Varian Inova 500 MHz spectrometers. All chemical shifts were reported in parts per million (δ) and were internally referenced to residual protio solvents unless otherwise noted. Spectral data were reported as follows: chemical shift (multiplicity [singlet (s), doublet (d), triplet (t), quartet (q), pentet (p), and multiplet (m)], coupling constants [Hz], integration). Carbon spectra were recorded with complete proton decoupling.

Conventional mass spectra were obtained using a Thermo Finnigan LEO Deca. Circular dichroism spectra were collected at 25° C. on an Aviv model 420 CD spectrophotometer using a 1 mm cuvette. Study compounds were dissolved in 50:50 hexanes:ethanol and spectra collected from 340 to 200 nm at 1 nm intervals using a 1 nm bandwidth and 1 s averaging time. Data were smoothed in the Aviv CDS Software. Background-subtracted spectra were normalized to PMT voltage at 285 nm to account for minor concentration differences.

N-chlorosuccinimide and N-bromosuccinimide were recrystallized from water. For cross-coupling conditions, 1,4-dioxane and deionized water were degassed three times by freeze-pump-thaw method before use. All other commercial reagents purchased from Sigma Aldrich, TCI, Frontier Scientific, Acros Organics, Strem, Oakwood, and Fisher were used as received without further purification. All flash column chromatography (FCC) was performed using Grade 60 Silica Gel (230-400 mesh) purchased from Fisher Scientific.

General Synthetic Route:

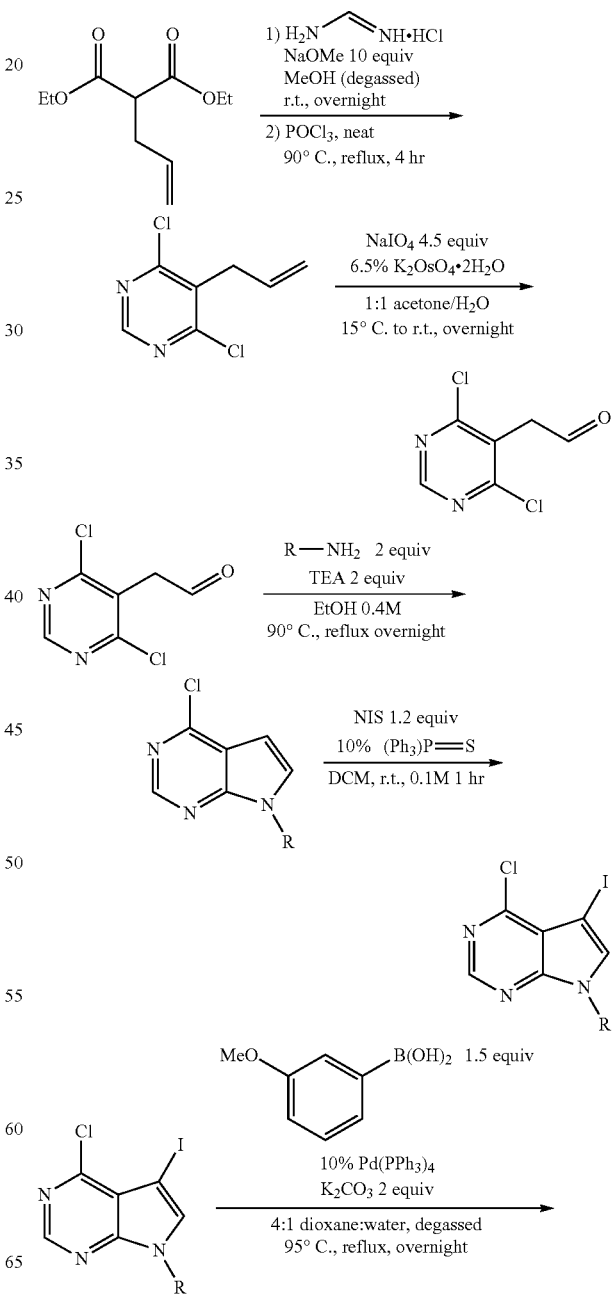

-continued

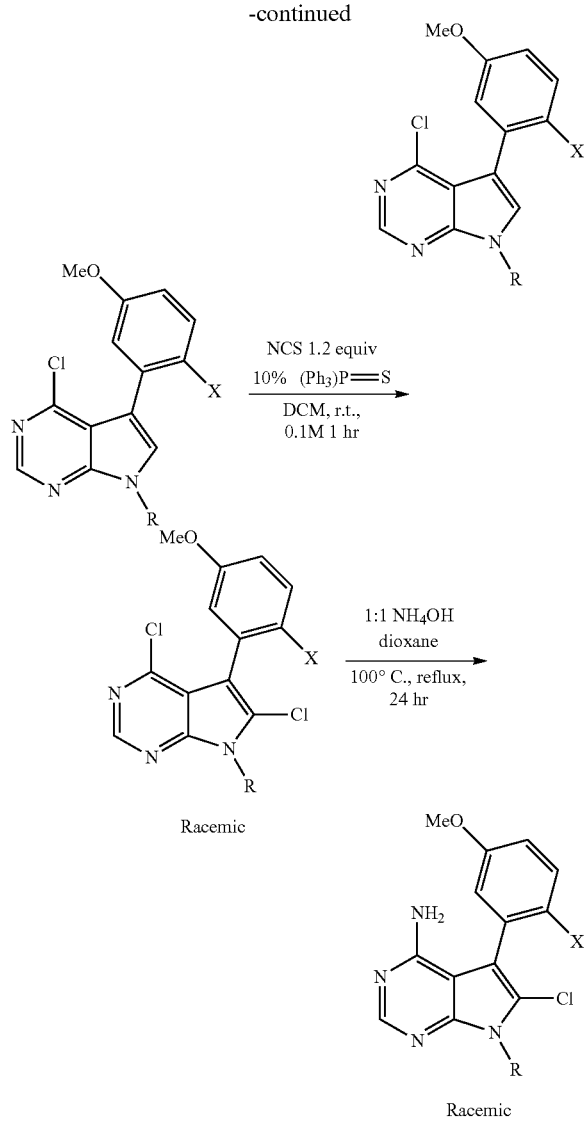

Racemic

As would be readily recognized by one of skill in the art, other atropisomerism rotational blocking moieties can be installed by varying the position ortho, meta, or para to OMe on the boronic acid) or the identity of X (e.g., X=($C_1$-$C_8$) alkyl, ($C_3$-$C_8$)cycloalkyl, or halo). The methoxy group on the boronic acid can also be other alkoxy groups, such as ($C_1$-$C_4$)alkoxy, or the oxygen can have a protecting group that when removed provides a hydroxyl group (—OH). Suitable boronic acid starting materials can be obtained from commercial suppliers such as Sigma-Aldrich, Alfa Aesar, and Boron Molecular, or by standard synthetic techniques known to those of skill in the art.

Synthesis of
2-(4,6-dichloropyrimidin-5-yl)acetaldehyde

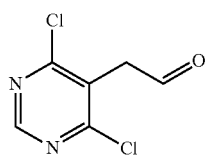

2-(4,6-dichloropyrimidin-5-yl)acetaldehyde was prepared by substantially following the procedure of Andrews et al., WO 2012/137089 A1, pages 206-208.

A solution of sodium methoxide (1.0 M in degassed Methanol, 1.0 equiv) was treated with formamidine hydrochloride (1.0 equiv) under nitrogen atmosphere. The mixture was stirred at room temperature for 5 minutes. Diethylallylmalonate was then added to the reaction mixture and stirred at room temperature overnight. The methanol was then evaporated in vacuo and the crude mixture was dissolved in minimal DI water and brought to pH 6 using concentrated HCl by drop-wise addition. Dichloromethane was then added to the reaction mixture, and the organic phase was extracted and filtered through diatomaceous earth. The solvent was then evaporated by rotovap to afford crude 5-allyl-6-hydroxy-3H-pyrimidin-4-one which was taken on without further purification.

5-allyl-6-hydroxy-3H-pyrimidin-4-one (1.0 equiv) was then treated with phosphorus oxychloride (4.1 equiv, neat) under an argon atmosphere. The mixture was heated at reflux (4 hours, 90° C.) and then cooled to room temperature. Ice-cold DI water was added drop-wise to the reaction mixture with vigorous stirring until all phosphorus oxychloride was quenched. The mixture was extracted with dichloromethane. The combined organic layers were washed with saturated aqueous sodium bicarbonate and brine, dried over sodium sulfate, filtered and concentrated to afford 5-allyl-4,6-dichloropyrimidine as a light yellow oil in 70.0 yield. $^1$H NMR matched literature. $^1$H NMR (400 MHz, DMSO-$d_6$) δ 8.81 (s, 1H), 6.04-5.7:2 (m, 1H), 5.28-4.87 (m, 2H), 3.72-3.49 (m, 2H).

5-allyl-4,6-dichloropyrimidine (1.0 equiv) was added to a 1:1 mixture of acetone and water (0.191M, 15° C.). Potassium osmate dihydrate was added (0.065 equiv) followed by four sequential additions of sodium meta-periodate in a one-hour period (4.53 equiv). The reaction mixture was stirred at room temperature for one hour. The suspension was then filtered and acetone was removed from the filtrate in vacuo. The desired product was extracted from the aqueous layer with dichloromethane, and the combined organic layers were washed with 10% sodium thiosulfate and brine, dried over sodium sulfate, filtered and concentrated to afford 2-(4,6-dichloropyrimidin-5-yl)acetaldehyde as a light amber solid (70% yield). $^1$H NMR match literature. $^1$H NMR (400 MHz, CDCl$_3$) δ 9.80 (s, 1H), 8.74 (s, 1H), 4.15 (s, 2H).

General Procedure to Synthesize N-alkylated Pyrrolopyrimidine (1a, 2a):

N-Alkylate PPYs were synthesized according to the procedures of Andrews et al., WO 2012/137089 A1, Prep 5.

1a. Synthesis of 4-chloro-7-cyclopentyl-7H-pyrrolo[2,3-d]pyrimidine

2-(4,6-dichloropyrimidin-5-yl)acetaldehyde was dissolved in ethanol (0.55 M). Triethylamine was then added to the reaction mixture (2 equiv) and stirred for ten minutes at room temperature. Cyclopentylamine (2 equiv) was then added to the reaction mixture and heated (reflux, 90° C.) overnight. The reaction mixture was evaporated in vacuo and diluted with 4:6 deionized water:ethyl acetate and the organic layer was collected and concentrated. The organic extract was then purified by FCC (gradient of hexanes:ethyl acetate (95:5 to 80:20) to yield a yellow oil in 32.9% Yield. $^1$H NMR (500 MHz, CDCl$_3$) δ 8.61 (s, 1H), 7.31 (d, J=3.6 Hz, 1H), 6.59 (d, J=3.6 Hz, 1H), 5.26-5.11 (m, 1H), 2.36-2.17 (m, 2H), 1.96-1.70 (m, 6H).

2a. Synthesis of 7-(tert-butyl)-4-chloro-7H-pyrrolo[2,3-d]pyrimidine

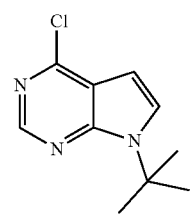

2-(4,6-dichloropyrimidin-5-yl)acetaldehyde was dissolved in ethanol (0.55M). Triethylamine was then added to the reaction mixture (2 equiv) and stirred for ten minutes at room temperature. Tert-butylamine was then added (2 equiv) to the reaction mixture and heated (reflux, 90° C.) overnight. The reaction mixture was then evaporated in vacuo. The crude mixture was then dissolved in 1:1 deionized water ethyl acetate and the organic layer was collected and concentrated. The organic extract was then purified using FCC (gradient of hexanes:ethyl acetate (95:5 to 80:20) to yield a yellow oil in 59.5% Yield. $^1$H NMR matched literature (Andrews et al, Patent WO2012137089 A1, Prep 5). $^1$H NMR (400 MHz, CDCl$_3$) δ 8.57 (s, 1H), 7.35 (d, J=3.7 Hz, 1H), 6.49 (d, J=3.7 Hz, 1H), 1.75 (s, 9H).

General Procedure for Lewis Base Catalyzed Iodination of N-alkylated Pyrrolopyrimidine (1b, 2b):

1b. Synthesis of 4-chloro-7-cyclopentyl-5-iodo-7H-pyrrolo[2,3-d]pyrimidine

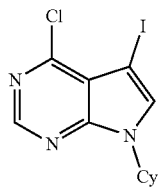

1a was dissolved in DCM at r.t. (0.1M). Triphenylphosphinesulfide (0.1 equiv) was then added and the reaction mixture was stirred for five minutes followed by the addition of N-iodosuccinimide (1.2 equiv). The reaction mixture was then stirred at room temperature for one hour. Dichloromethane was then evaporated in vacuo and the reaction mixture was dissolved in 4:6 deionized water:ethyl acetate and the organic layer was collected and concentrated. The organic extract was then purified using FCC (gradient of hexanes:ethyl acetate (95:5 to 80:20) to yield a white solid in 77.5% Yield. NMR (500 MHz, CDCl$_3$) δ 8.59 (s, 1H), 7.44 (s, 1H), 5.20 (p, J=7.4 Hz, 1H), 2.24 (m, 2H), 1.96-1.74 (m, 6H).

2b. Synthesis of 7-(tert-butyl)-4-chloro-5-iodo-7H-pyrrolo[2,3-d]pyridine

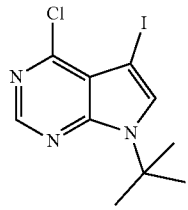

2a was dissolved in DCM at r.t. (0.1M). Triphenylphosphinesulfide (0.1 equiv) added and the reaction mixture was stirred for five minutes followed by the addition of N-iodosuccinimide (1.2 equiv). The reaction mixture was then stirred at room temperature for one hour. Dichloromethane was then evaporated in vacuo and the reaction mixture was dissolved in 4:6 deionized water:ethyl acetate and the organic layer was collected and concentrated. The organic extract was then purified using FCC (gradient of hexanes: ethyl acetate (95:5 to 80:20) to yield a white solid in 75% Yield. $^1$H NMR matched literature (Maddox, Sean M. et al, Organic Letters, 17(4), 1042-1045; 2015) $^1$H NMR (500 MHz CDCl$_3$) δ 8.60 (s, 1H), 7.50 (s, 1H), 1.77 (s, 9H).

Cross-Coupling Procedure (1c, 1d, 2c, 2d):

1c. Synthesis of 4-chloro-5-(2-chloro-5-methoxyphenyl)-7-cyclopentyl-7H-pyrrolo[2,3d]pyrimidine

1b (210 mg, 0.62 mmol) was combined with (2-chloro-5-methoxyphenyl)boronic acid (175 mg, 0.94 mmol), Tetrakis(triphenylphosphine)palladium (72 mg, 0.06:2 mmol), and potassium carbonate (173 mg, 1.25 mmol). Upon purging with argon gas the mixture was dissolved in a 4:1 mixture of degassed dioxane/DI water (0.25M) and kept inert argon atmosphere. The reaction mixture was then heated at, 95° C. for 48 h. Volatiles were then evaporated in vacuo and the reaction mixture was dissolved in 4:6 DI water:ethyl acetate and the organic layer was collected and concentrated. The organic extract was then purified using FCC (gradient of hexanes:ethyl acetate 95:5 to 80:20) to yield 39 mg of an orange oil in 35% Yield. $^1$H NMR (599 MHz, CDCl$_3$) δ 8.64 (s, 1H), 7.37 (d, J=8.8 Hz, 1H), 7.33 (s, 1H), 6.95 (d, J=3.0 Hz, 1H), 6.88 (dd, J=8.8, 3.1 Hz, 1H), 5.32-5.26 (m, 1H), 3.82 (s, 3H), 2.36-2.24 (m, 2H), 2.05-1.89 (m, 4H), 1.86-1.76 (m, 2H). $^{13}$C NMR (151 MHz, CDCl$_3$) δ 157.68, 152.10, 151.00, 150.39, 132.80, 129.87, 126.46, 125.96, 118.38, 115.81, 114.88, 113.13, 55.93, 55.57, 32.89, 24.13.

1d. Synthesis of 5-(2-bromo-5-methoxyphenyl)-4-chloro-7-cyclopentyl-7H-pyrrolo[2,3-d]pyrimidin

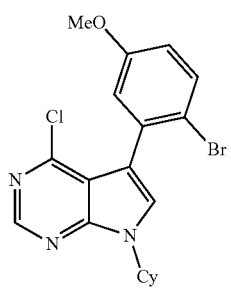

1b (200 mg, 0.6 minor) was combined with (2-promo-5-methoxyphenyl)boronic acid (206 mg, 0.9 mmol), Tetrakis(triphenylphosphine)palladium (69 mg, 0.06 mmol), and potassium carbonate (165 mg, 1.2 mmol). Upon purging with argon gas the mixture was dissolved in a 4:1 mixture of degassed dioxane/DI water (0.25M) and kept under inert argon atmosphere. The reaction mixture was then heated at 95° C. for 48 h. Dioxane was then evaporated in vacuo and the reaction mixture was dissolved in 4:6 DI water:ethyl acetate and the organic layer was collected and concentrated. The organic extract was then purified by FCC (gradient of hexanes:ethyl acetate 95:5 to 80:20) to yield 139 mg of an orange oil in 57% % Yield. $^1$H NMR (400 MHz, CDCl$_3$) δ 8.62 (s, 7.51 (d, J=8.8 Hz, 1H), 7.31 (s, 1H), 6.94 (d, J=3.1 Hz, 1H), 6.79 (dd, J=8.8, 3.1 Hz, 1H), 5.31-5.21 (m, 1H), 3.78 (s, 3H), 2.32-2.21 (m, 2H), 1.96-1.86 (m, 4H), 1.84-1.73 (m, 2H). $^{13}$C NMR (126 MHz, CDCl$_3$) δ 158.30, 152.03, 150.89, 150.40, 134.8, 132.93, 125.97, 118.53, 116.17, 115.68, 115.29, 114.92, 55.93, 55.53, 32.92, 24.16.

2c. Synthesis of 7-(tert-butyl)-4-chloro-5-(2-chloro-5-methoxyphenyl)-7H-pyrrolo[2,3-d]pyrimidine

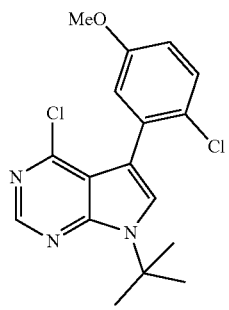 [SMILES: COc1ccc(Cl)c(-c2cn(C(C)(C)C)c3ncnc(Cl)c23)c1]

2b (189 mg, 0.55 mmol) was combined with (2-chloro-5-methoxyphenyl)boronic acid (152 mg, 0.82 mmol), Tetrakis(triphenylphosphine)palladium (63 mg, 0.055 mol), and potassium carbonate (150 mg, 1.1 mmol). Upon purging with argon gas the mixture was dissolved in a 4:1 mixture of degassed dioxane:DI water (0.25M) and kept under inert argon atmosphere. The reaction mixture was then heated at 95° C.) for 48 h. Dioxane was then evaporated in vacuo and the reaction mixture was dissolved in 4:6 DI water:ethyl acetate and the organic layer was collected and concentrated. The organic extract was then purified by FCC (gradient of hexanes:ethyl acetate 95:5 to 80:20) to give 81 mg of a yellow oil in 43% Yield. $^1$H NMR (400 MHz, CDCl$_3$) δ 8.63 (s, 1H), 7.48-7.30 (m, 2H), 6.94 (d, J=3.0 Hz, 1H), 6.87 (dd, J=8.8, 3.1 Hz, 1H), 3.81 (s, 3H), 1.83 (s, 9H). $^{13}$C NMR (101 MHz, CDCl$_3$) δ 157.67, 152.12, 150.99, 149.37, 133.14, 129.79, 126.62., 126.46, 118.35, 116.86, 114.81, 111.77, 58.02, 55.55, 29.24.

2d. Synthesis of 5-(2-bromo-5-methoxyphenyl)-7-(tert-butyl-4-chloro-7H-pyrrolo[2,3-d]pyrimidine

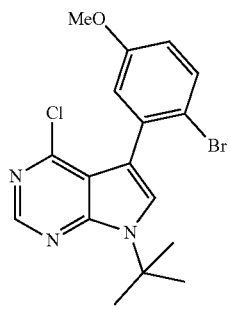 [SMILES: COc1ccc(Br)c(-c2cn(C(C)(C)C)c3ncnc(Cl)c23)c1]

2b (179 mg, 0.52 mmol) was combined with (2-bromo-5-methoxyphenyl)boronic acid (178 mg, 0.77 mmol), Tetrakis(triphenylphosphine)palladium (60 mg, 0.052 mmol), and potassium carbonate (142 mg, 1.05 mmol). Upon purging with argon gas the mixture was dissolved in a 4:1 mixture of degassed dioxane:DI water (0.25M) and kept under inert argon atmosphere. The reaction mixture was then heated at 95° C. for 48 h. Dioxane was then evaporated in vacuo and the reaction mixture was dissolved in 4:6 DI water:ethyl acetate and the organic layer was collected and concentrated. The organic extract was then purified by FCC (gradient of hexanes:ethyl acetate 95:5 to 80:20) to give 124 mg of a yellow oil in 61% Yield, $^1$H NMR (400 MHz. CDCl$_3$) δ 8.62 (s, 1H), 7.51 (d, J=8.8 Hz, 1H), 7.36 (s, 1H), 6.94 (d, J=3.1 Hz, 1H), 6.80 (dd, J=8.8, 3.1 Hz, 1H), 3.79 (s, 3H), 1.82 (s, 9H). $^{13}$C NMR (101 MHz, CDCl$_3$) δ 158.28, 152.07, 150.88, 149.39, 135.22., 132.85, 126.41, 118.49, 116.72, 116.37, 115.22, 113.58, 58.00, 55.51, 29.26.

1c-Cl. Synthesis of 4,6-dichloro-5-(2-chloro-5-methoxyphenyl)-7-cyclopentyl-7H-pyrrolo[2,3-d]pyrimidine

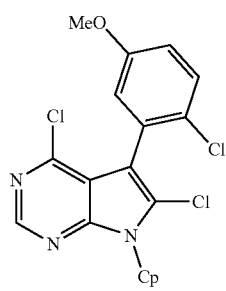

1c (39 mg, 0.11 mmol) was dissolved in DCM at r.t. (0.1M). Triphenyl-phosphinesulfide (4 mg, 0.013 mmol) was added and the reaction mixture was stirred for five minutes followed by the addition of N-chlorosuccinimide (18 mg, 0.135 mmol). The reaction mixture was then stirred at room temperature for one hour. Dichloromethane was then evaporated in vacuo and the reaction mixture was dissolved in 4:6 DI water:ethyl acetate and the organic layer was collected and concentrated. The organic extract was then purified by FCC (gradient of hexanes:ethyl acetate 95:5 to 80:20) to yield a light yellow solid in 83% Yield. $^1$H NMR (400 MHz, CDCl₃) δ 8.61 (s, 1H), 7.39 (dd, J=8.6, 0.6 Hz, 1H), 6.97-6.88 (obs m, 2H), 5.33-5.19 (m, 1H), 3.82 (s, 3H), 2.56-2.35 (m, 2H), 2.21-2.04 (m, 4H), 1.83-1.67 (m, 2H). ¹³C NMR (101 MHz, CDCl₃) δ 157.82, 150.97, 150.07, 131.04, 129.90, 127.77, 127.14, 118.34, 115.77, 115.66, 110.06, 104.99, 56.83, 55.58, 30.59, 24.98

Synthesis of 5-(2-bromo-5-methoxyphenyl)-4,6-dichloro-7-cyclopentyl-7H-pyrrolo[2,3-d]pyrimidine

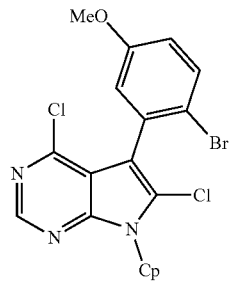

1d (139 mg, 0.34 mmol) was dissolved in DCM at r.t. (0.1M). Triphenylphosphinesulfide (11 mg, 0.037 mmol) was added and the reaction mixture was stirred for five minutes followed by the addition of N-chlorosuccinimide (55 mg, 0.41 mmol). The reaction mixture was then stirred at room temperature for one hour. Dichloromethane was then evaporated in vacuo and the reaction mixture was dissolved in 4:6 DI water:ethyl acetate and the organic layer was collected and concentrated. The organic extract was then purified by FCC (gradient of hexanes:ethyl acetate 95:5 to 80:20) to yield 130 mg of a light yellow solid in 79% Yield. ¹H NMR (400 MHz, CDCl₃) δ 8.62 (s, 1H), 7.51 (d, J=8.8 Hz, 1H), 6.94 (d, J=3.1 Hz, 1H), 6.79 (dd, J=8.8, 3.1 Hz, 1H), 5.32-5.22 (m, 1H), 3.78 (s, 3H), 2.38-2.20 (m, 2H), 2.00-1.85 (m, 4H), 1.84-1.71 (m, 2H). ¹³C NMR (126 MHz, CDCl₃) δ 158.30, 152.03, 150.89, 150.40, 134.88, 132.93, 125.97, 118.53, 116.17, 115.68, 115.29, 114.92, 55.93, 55.53, 32.92, 24.16.

2e-Cl. Synthesis of 7-(tert-butyl)-4,6-dichloro-5-(2-chloro-5-methoxyphenyl)-7H-pyrrolo[2,3d]pyrimidine

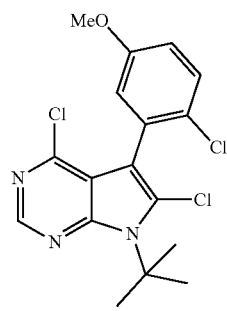 [SMILES: COc1ccc(Cl)c(-c2c(Cl)n(C(C)(C)C)c3ncnc(Cl)c23)c1]

2c (81 mg, 0.22 mmol) was dissolved in DCM at r.t. (0.1M). Triphenylphosphinesulfide (7 mg, 0.024 mmol) was added and the reaction mixture was stirred for five minutes followed by the addition of N-chlorosuccinimide (38 mg, 0.28 mmol). The reaction mixture was then stirred at room temperature for one hour. Dichloromethane was then evaporated in vacuo and the reaction mixture was dissolved in 4:6 DI water:ethyl acetate and the organic layer was collected and concentrated. The organic extract was then purified by FCC (gradient of hexanes:ethyl acetate 95:5 to 80:20) to yield 76 mg of a yellow amorphous solid in 79% Yield. 1H NMR (400 MHz, CDCl₃) δ 8.59 (s, 1H), 7.38 (d, J=8.8 Hz, 1H), 6.92 (dd, J=8.8, 3.1 Hz, 1H), 6.88 (d, J=3.0 Hz, 1H), 3.81 (s, 3H), 2.02 (s, 9H). ¹³C NMR (101 MHz, CDCl₃) δ157.80, 151.45, 150.77, 149.22, 131.60, 129.80, 128.24, 127.18, 118.30, 115.75, 115.59, 112.10, 63.60, 55.58, 31.22.

2d-Cl. Synthesis of 5-(2-bromo-5-methoxyphenyl)-7-(tert-butyl)-4,6-dichloro-7H-pyrrolo[2,3-d]pyrimidine

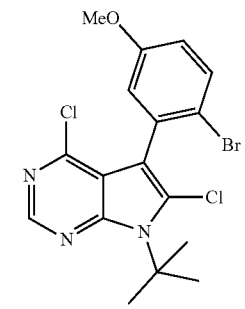

2d (124 mg, 0.314 mmol) was dissolved in DCM at r.t. (0.1M). Triphenylphosphinesulfide (10 mg, 0.034 mmol) was added and the reaction mixture was stirred for five minutes followed by the addition of N-chlorosuccinimide (51 mg, 0.38 mmol). The reaction mixture was then stirred at room temperature for one hour. Dichloromethane was then evaporated in vacuo and the reaction mixture was dissolved in 4:6 DI water:ethyl acetate and the organic layer was collected and concentrated. The organic extract was then purified by FCC (gradient of hexanes:ethyl acetate 95:5 to 80:20) to yield 96 mg of a yellow solid in 66% Yield. ¹H NMR (500 MHz, CDCl₃) δ 8.60 (s, 1H), 7.57 (d, J=8.8 Hz, 1H), 6.91 (d, J=3.0 Hz, 1H), 6.88 (dd, J=8.8, 3.1 Hz, 1H), 3.82 (s, 3H), 2.04 (s, 9H). ¹³C NMR (126 MHz, CDCl₃) δ 158.51, 151.40, 150.78, 149.26, 133.81, 132.8, 128.17, 118.46, 116.74, 115.95, 115.63, 114.00, 63.58, 55.55, 31.26.

Amination Procedure towards 1e, 1f, 2e, 2f:

1.f 5-(2-bromo-5-methoxyphenyl)-6-chloro-7-cyclopentyl-7H-pyrrolo[2,3-d]pyrimidin-4-amine

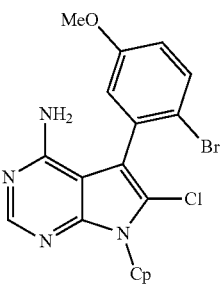

1d-Cl (130 mg, 0.3 mmol) was dissolved in 3 mL of a 1:1 mixture of dioxane and 28% ammonium hydroxide (0.6 M with respect to 1d-Cl) and heated under reflux (100° C., 24 hours) with vigorous stirring. The reaction was concentrated in vacuo and a 1:1 separation of the reaction mixture was performed with DI water:ethyl acetate and the organic layer was concentrated to give 119 mg crude racemic if as a light yellow crystalline solid in 96% yield. The atropisomers of 1f then separated by chiral semi-preparative HPLC (80% alcohol in Hexanes, 3 mL per minute, Chiral IA-column 10 mm×250 mm). ¹H NMR (500 MHz, CDCl₃) δ 8.20 (s, 1H), 7.54 (d, J=8.8 Hz, 1H), 6.87 (d, J=3.0 Hz, 1H), 6.82 (dd, J=8.8, 3.1 Hz, 1H), 5.24-5.13 (m, 1H), 4.99 (br s, 2H), 3.75

(s, 3H), 2.60-2.14 (m, 2H), 2.14-1.83 (m, 4H), 1.82-1.41 (m, 2H) $^{13}$C NMR (126 MHz, CDCl$_3$) δ 158.97, 155.04, 149.94, 148.91, 134.10, 133.89, 117.85, 116.45, 115.70, 112.19, 111.42, 93.30, 56.16, 55.62, 30.65, 24.95. MS: calculated for C$_{18}$H$_{18}$BrClN$_4$O 422.03. Observed. [M+H]$^+$: 423.00

2e. Synthesis of 7-(tert-butyl)-6-chloro-5-(2-chloro-5-methoxyphenyl)-7H-pyrrolo[2,3d]pyrimidin-4-amine

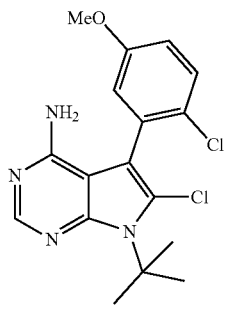 [SMILES: COc1ccc(Cl)c(-c2c(Cl)n(C(C)(C)C)c3ncnc(N)c23)c1]

2c-Cl (76 mg, 0.20 mmol) was dissolved in 3 mL of a 1:1 mixture of dioxane and 28% ammonium hydroxide (0.6 M with respect to 2c-Cl) and heated under reflux (100° C., 24 hours) with vigorous stirring. The reaction was concentrated in vacuo and a 1:1 separation of the reaction mixture was performed with DI water:ethyl acetate and the organic layer was concentrated to give 71 mg of crude racemic 2e as a medium yellow amorphous solid in 98% % yield. The atropisomers of 2e were then separated by chiral semi-preparative HPLC (50% alcohol in Hexanes, 3 mL per minute, Chiral IA-column 10 mm×250 mm). $^1$H NMR (500 MHz, CDCl$_3$) δ 8.27 (s, 1H), 7.45 (d, J=8.6 Hz, 1H), 6.97 (d, J=3.1 Hz, 1H), 6.95 (dd, J=5.7, 3.0 Hz, 1H), 4.89 (s, 2H), 3.84 (s, 3H), 2.02 (s, 9H). $^{13}$C NMR (126 MHz, CDCl$_3$) δ 158.28, 155.18, 150.58, 149.47, 132.54, 130.67, 126.59, 122.52, 117.67, 116.06, 111.24, 102.48, 62.64, 55.65, 31.29. MS: calculated for C$_{17}$H$_{18}$Cl$_2$N$_4$O 364.09. Observed [M+H]$^+$; 365.00

2f. Synthesis of 5-(2-bromo-5-methoxyphenyl)-7-(tert-butyl)-6-chloro-7H-pyrrolo[2,3-d]pyrimidin-4-amine

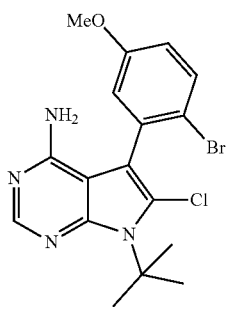 [SMILES: COc1ccc(Br)c(-c2c(Cl)n(C(C)(C)C)c3ncnc(N)c23)c1]

2d-Cl. (96 mg, 0.22 mmol) was dissolved in 3 of a 1:1 mixture of dioxane and 28% ammonium hydroxide (0.6 M with respect to 2d-Cl) and heated under reflux (100° C., 24 hours) with vigorous stirring. The reaction was concentrated in vacuo and a 1:1 separation of the reaction mixture was performed with DI water:ethyl acetate and the organic layer was concentrated to give 89 mg crude racemic 2f as a yellow solid in 97% yield. The atropisomers of 2f were then separated by chiral semi-preparative HPLC (50% alcohol in Hexanes, 3 mL per minute, Chiral IA-column 10 mm×250 mm). In NMR (500 MHz, CDCl$_3$) δ 8.07 (s, 1H), 7.58 (d, J=8.9 Hz, 1H), 6.88 (dd, J=8.9, 3.0 Hz, 1H), 6.82 (d, J=3.0 Hz, 1H), 5.23 (s, 2H), 3.76 (s, 3H), 1.93 (s, 9H). $^{13}$C NMR (126 MHz, CDCl$_3$) δ 159.36, 150.67, 147.44, 138.50, 134.38, 131.92, 125.69, 117.66, 117.28, 115.63, 115.12, 100.88, 65.02, 55.72, 31.28. MS: calculated for C$_{17}$H$_{18}$BrClN$_4$O 409.71 Observed [M+H]$^{30}$: 410.93

1e. Synthesis of 6-chloro-5-(2-chloro-5-methoxyphenyl)-7-cyclopentyl-7H-pyrrolo[2,3-d]pyrimidin-4-amine

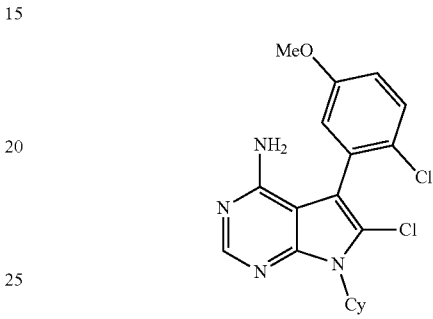

1c-Cl (20 mg, 0.05 mmol) was dissolved in 1 mL of a 1:1 mixture of dioxane and 28% ammonium hydroxide (0.6 M with respect to 1c-Cl) and heated under reflux (130° C., 24 hours) with vigorous stirring. The reaction was concentrated in vacuo and a 1:1 separation of the reaction mixture was performed with DI water:ethyl acetate and the organic layer was concentrated to give 15 mg of 1e isolated as a yellow solid in 81% Yield. The atropisorners of 2f were then separated by chiral semi-preparative HPLC (50% alcohol in Hexanes, 3 mL per minute, Chiral IA-column). $^1$H NMR (599 MHz, CDCl$_3$) δ 8.25 (s, 1H), 7.43 (d, J=8.7 Hz, 1H), 6.95-6.91 (obs m, 2H), 5.29-5.17 (m, 2H), 3.81 (s, 3H), 2.51-2.28 (m, 2H), 2.17-1.99 (m, 4H), 1.78-1.62 (m, 2H). $^{13}$C NMR (151 MHz, CDCl$_3$) δ 160.98, 157.34, 151.69, 151.38, 134.30, 133.52, 128.89, 125.14, 120.22, 118.78, 112.33, 104.55, 58.89, 58.31, 33.40, 27.60. MS: calculated for C$_{18}$H$_{18}$Cl$_2$N$_4$O 376.09 Observed [M+H]$^+$: 377.13.

Control compound 5 was synthesized in an analogous manner.

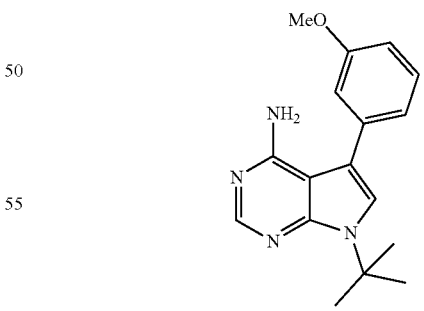

$^1$H NMR (400 MHz, CDCl$_3$) δ 8.24 d(s, 1H), 7.29 (t, 1H), 7.03 (s, 1H), 7.02-6.96 (m, 1H), 6.96-6.91 (m, 1H), 6.86-6.78 (m, 1H), 5.12 (s, 2H), 3.78 (s, 3H), 1.73 (s, 9H). MS: calculated for C$_{17}$H$_{20}$N$_4$O 296.16 Observed [M+H]$^+$: 297.20.

Control compound 6 was synthesized in an analogous manner.

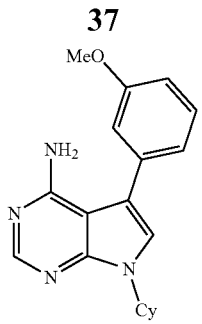

$^1$H NMR (400 MHz, CDCl$_3$) δ 8.31 (s, 1H), 7.35 (t, 1H), 7.07-7.04 (m, 1H), 7.03 (s, 1H), 7.01 (q, J=2.5, 1.6 Hz, 1H), 6.88 (dd, J=8.3, 2.6, 0.9 Hz, 1H), 5.41 (s, 2H), 5.25-5.15 (m, 1H), 3.84 (s, 3H), 2.31-2.17 (m, 2H), 1.95-1.83 (m, 4H) 1.81-1.68 (m, 2H). MS: calculated for C$_{18}$H$_{20}$N$_4$O 308.16 Observed [M+H]$^+$: 309.27.

Example 2. Compound Evaluation and Analysis

A. Experimental Measurement of the Barriers to Rotation

Enantiomerically enriched atropisomeric pyrrolopyrimidine analogues were isolated via chiral HPLC (Daicel Chiralpak IA PN:80335, 3 mL/min, 80:20 or 50:50 hexanes:ethanal, 25° C.) and evaporated in vacuo. The enantiomerically enriched analogues were then dissolved in ethanol and placed in a sealed 2-dram vial and heated under constant temperature on an aluminum block. At each time point, an aliquot of the mixture was removed and quenched in an HPLC vial containing ice cold 80:20 hexanes:ethanol. Each sample was then injected into the chiral HPLC system (Daicel Chiralpak IA PN:80325, 1 mL/min, 80:20 or 50:50 hexanes:ethanol, 25° C.) and enantiomeric excess (ee) measured. The timepoint and enantiomeric excess (ee) data was then plotted in order to determine an observed rate constant, $k_{obs}$, at the corresponding temperature. The barrier to rotation was then calculated using the relationship of $k_{racemization}=2*k_{enantiomerization}$ and then substituted into the Gibbs Free Energy Equation:

$$\Delta G = -RT\ln\left(\frac{hk}{\kappa k_b T}\right) \quad k = \left(\frac{\ln(2)}{t_{\frac{1}{2}}(s)}\right)$$

where h=Planck Constant, $k_b$=Boltzmann Constant, T=Temp. (K), R=Gas Constant.

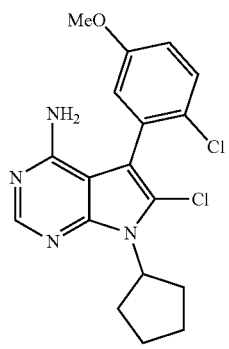

1e

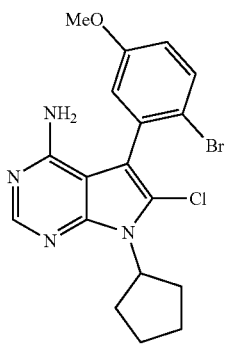

1f

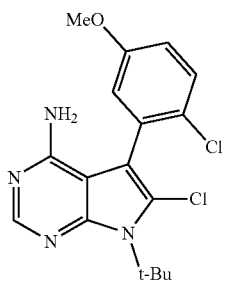

2e

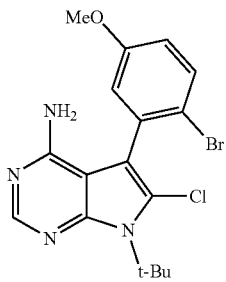

2f

| Barrier to Rotation | 1e | 1f | 2e | 2f |
|---|---|---|---|---|
| $k_{obs}$ | 1.24E-04 | 1.01E-05 | 3.27E-05 | 2.68E-05 |
| kcal/mol | 27.2 | 29.0 | 28.6 | 30.4 |
| $t_{1/2}$ to Racemization at 37° C. (Days) | 18 | 301 | 157 | 2929 |
| (Years) | n/a | 0.826 | 0.429 | 8.02 |

B. Kinase Profiling Data

All samples were sent out to Life Technologies to obtain kinase inhibition data. A brief description of the assays and analyses are included below.

Assay Theory (SelectScreen® Kinase Profiling Services (Life Technologies, Madison, Wis. USA). The Z'-LYTE® biochemical assay employs a fluorescence-based, coupled-enzyme format and is based on the differential sensitivity of phosphorylated and non-phosphorylated peptides to proteolytic cleavage. The peptide substrate is labeled with two fluorophores one at each end—that make up a FRET pair.

In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides.

Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress, as shown in the equation below:

$$\text{Emission Ratio} = \frac{\text{Coumarin Emission (445 nm)}}{\text{Fluorescein Emission (520 nm)}}$$

A significant benefit of this ratiometric method for quantitating reaction progress is the elimination of well-to-well variations in FRET-peptide concentration and signal intensities. As a result, the assay yields very high Z'-factor values (>0.7) at a low percent phosphorylation. Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will he high if the FRET-peptide is non-phosphorylated (i.e., kinase inhibition).

Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

C. In Silica Docking Methodology

The x-ray crystal structures of: Src in complex with inhibitor CGP77675 (PDB 1YOL); Ret in complex with inhibitor PP1 (PDB 2IVV); the active form of EGFR in complex with an ATP analogue (PDB 2GS6) as well as the inactive form of EGFR in complex with AMP-PNP (PDB 2GS7) were used for these studies. Each x-ray structure was imported into MOE (Chemical Computing Group) and structurally aligned using the Align and Superpose functions in MOE. All waters as well as other non-protein, non-ligand, or non-cofactor molecules were removed and the structures were protonated.

Compounds 5 and 2e were drawn using Chemdraw (Cambridgesoft, Inc.) and then imported into MOE. The two-dimensional structures were converted to three-dimensional structures and were minimized using the MMFF94x gas phase potential (Halgren, T. A., *J. Comp. Chem.*, 1996, 17, 490-512). For each protein, the x-ray conformation of the bound ligand was used to define the binding pocket. Docking experiments were performed with the Dock function in MOE using the Ambe 12:EHT forcefield (Gerber and Müller, *J. Comput. Aided Mol. Des.*, 1995, 3, 251-68) with parameterized solvation and default parameters and fitness functions. For these studies the receptor binding site remained rigid and the ligand was allowed full flexibility with the top ten scoring, non-redundant poses retained. In order to verify that poses resulting from in silico docking represent correctly bound conformations, each pose was visually inspected and compared to the experimentally determined binding modes and conformations for each protein respectively. Additionally, the dihedral angles made by the two aryl rings for each top scoring pose are reported.

D. Rotational Landscape Calculations

All structures were optimized in the gas phase using density functional theory (RB3LYP) with the 6-31G(d) basis set as implemented in the Gaussian 09 suite of programs. The indicated dihedral angle was frozen every 10 degrees while the rest of the structure was minimized. Single point energy calculations were performed on the minimized structures using M06-2X/6-31+G(d) as implemented in Gaussian 09. RB3LYP/6-31G(d) thermal corrections were applied to the M06-2X/6-31+G(d) energies (Zhao, Y.; Truhlar, D. G. *Theor Chem Account* 2006, 120, 215; Frisch et al., *J. Chem. Phys.* 1984, 80, 3265). All energies are reported in kcal/mol with respect to the minimized inhibitor.

Example 3. Pharmaceutical Dosage Forms

The following formulations illustrate representative pharmaceutical dosage forms that may be used for the therapeutic administration of a compound (e.g., an atropisomer) of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

-continued

| (vii) Topical Gel 1 | wt. % |
|---|---|
| 'Compound X' | 5% |
| Carbomer 934 | 1.25% |
| Triethanolamine | q.s. |
| (pH adjustment to 5-7) | |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An atropisomer comprising Formula IA:

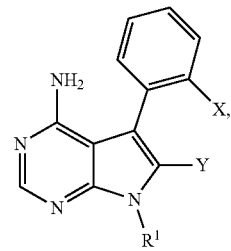

(IA)

or
an enantiomer, salt or solvate thereof;
wherein
X and Y taken together form an atropisomerism rotational blocking moiety wherein X and Y are not H; and
$R^1$ is a buttressing substituent selected from the group consisting of branched alkyl, linear alkyl, cycloalkyl and phenyl, wherein phenyl is optionally substituted;
wherein the atropisomer is atropisomerically stable.

2. An atropisomer of Formula I:

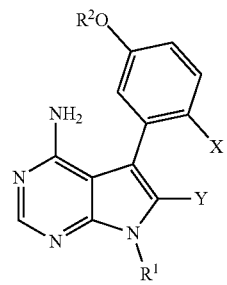

(I)

wherein
$R^1$ is $(C_1-C_8)$alkyl, $(C_3-C_8)$cycloalkyl, benzyl, or phenyl wherein phenyl is optionally substituted;
$R^2$ is H, $(C_1-C_4)$alkyl, or $(C_3-C_6)$cycloalkyl;
X is $(C_1-C_8)$alkyl, $(C_3-C_8)$cycloalkyl, or halo; and
Y is taken together with X to form an atropisomerism rotational blocking moiety, wherein Y is not H;
or salt or solvate thereof.

3. The atropisomer of claim 2 wherein $R^1$ is methyl, cyclopentyl, tert-butyl, iso-pentyl, or phenyl, and $R^2$ is H or Me.

4. The atropisomer of claim 2 wherein X is chloro, bromo, or methyl.

5. The atropisomer of claim 2 wherein Y is chloro.

6. The atropisomer of claim 2 wherein the atropisomer is an atropisomer of Formula X:

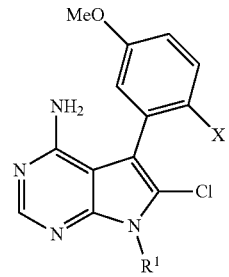

(X)

wherein

R[1] is cyclopentyl, tert-butyl, iso-pentyl, or phenyl; and

X is methyl, halo or (C$_3$-C$_8$)cycloalkyl;

or salt or solvate thereof.

7. The atropisomer of claim 6 wherein X is chloro or bromo.

8. The atropisomer of claim 6 wherein the atropisomer is:

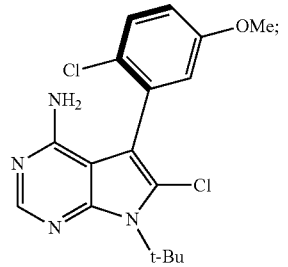

2e-(R)

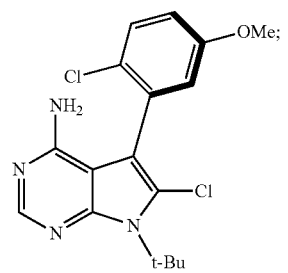

2e-(S)

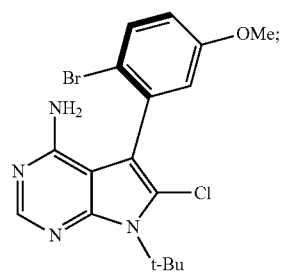

2f-(R)

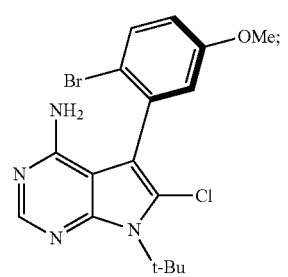

2f-(S)

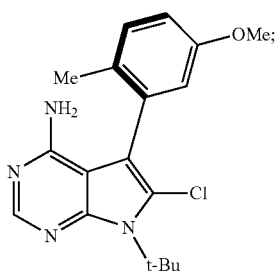

2m-(R)

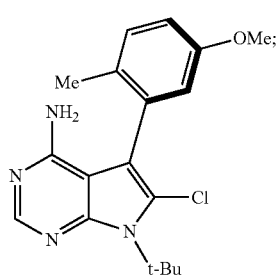

2m-(S)

or a salt or solvate thereof.

9. A pharmaceutical composition comprising the atropisomer of claim 2 in combination with a pharmaceutically acceptable diluent, carrier, or excipient.

10. A conformationally stable atropisomer of Formula X:

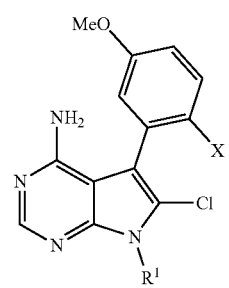

(X)

wherein

R[1] is cyclopentyl, tert-butyl, iso-pentyl, or phenyl wherein phenyl is optionally substituted; and X is an atropisomerism rotational blocking moiety, wherein the blocking moiety is chloro or bromo;

or salt or solvate thereof.

11. The atropisomer of claim 1 wherein the atropisomerism rotational blocking moiety of the atropisomer forms a barrier to rotation of about 27 kcal/mol to about 30 kcal/mole, and the atropisomer has a half-life of about 8 days to about 8 years.

12. The atropisomer of claim 2, wherein Y is chloro, bromo or methyl.

* * * * *